US011528924B2

(12) United States Patent
Golan

(10) Patent No.: US 11,528,924 B2
(45) Date of Patent: Dec. 20, 2022

(54) ALCOHOLIC BEVERAGE SUBSTITUTES

(71) Applicant: Clearmind Medicine Inc., Vancouver (CA)

(72) Inventor: Ezekiel Golan, Vancouver (CA)

(73) Assignee: Clearmind Medicine, Inc., Vancouver (CA)

( * ) Notice: Subject to any disclaimer, the term of this patent is extended or adjusted under 35 U.S.C. 154(b) by 0 days.

(21) Appl. No.: 15/534,121

(22) PCT Filed: Dec. 9, 2015

(86) PCT No.: PCT/IL2015/051194
§ 371 (c)(1),
(2) Date: Jun. 8, 2017

(87) PCT Pub. No.: WO2016/092547
PCT Pub. Date: Jun. 16, 2016

(65) Prior Publication Data
US 2017/0360067 A1    Dec. 21, 2017

Related U.S. Application Data

(60) Provisional application No. 62/089,504, filed on Dec. 9, 2014, provisional application No. 62/089,500, filed on Dec. 9, 2014.

(51) Int. Cl.
| | |
|---|---|
| A23L 2/38 | (2021.01) |
| A23L 2/52 | (2006.01) |
| C12G 3/06 | (2006.01) |
| A61K 31/135 | (2006.01) |
| A61P 25/32 | (2006.01) |
| C12G 3/08 | (2006.01) |

(52) U.S. Cl.
CPC ........... *A23L 2/382* (2013.01); *A23L 2/52* (2013.01); *A61K 31/135* (2013.01); *A61P 25/32* (2018.01); *C12G 3/06* (2013.01); *C12G 3/08* (2013.01)

(58) Field of Classification Search
CPC ..... A23L 2/52; C07C 211/42; C03D 295/096; C03D 317/70; C03D 319/18; C12G 3/08; C12G 3/021; C12G 3/022; C12G 3/023; C12G 3/024; C12G 3/025; A61K 31/135; C12H 3/00; C12H 3/02; C12H 3/04
See application file for complete search history.

(56) References Cited

U.S. PATENT DOCUMENTS

| | | | | |
|---|---|---|---|---|
| 1,256,894 A * | 2/1918 | Gudeman | ................ | A23L 3/24 |
| | | | | 99/277 |
| 1,302,551 A * | 5/1919 | Heuser | ................ | C12G 3/08 |
| | | | | 426/14 |
| 1,390,710 A * | 9/1921 | Heuser | ................ | C12G 3/025 |
| | | | | 426/14 |
| 1,401,700 A * | 12/1921 | Heuser | ................ | C12H 3/02 |
| | | | | 426/534 |
| 2,712,998 A * | 7/1955 | Vosseler | ................ | C12G 3/02 |
| | | | | 426/13 |
| 3,558,325 A * | 1/1971 | Recsei | ................ | C12H 1/14 |
| | | | | 426/534 |
| 4,990,350 A * | 2/1991 | Rohmann | ................ | C12H 3/04 |
| | | | | 426/330.4 |
| 5,708,018 A | 1/1998 | Haadsma-Svensson et al. | | |
| 6,472,009 B1 * | 10/2002 | Berrebi | ................ | C12H 3/00 |
| | | | | 426/330.4 |
| 6,933,410 B2 * | 8/2005 | Prashad | ................ | C07C 209/62 |
| | | | | 564/414 |
| 10,137,096 B2 | 11/2018 | Golan | | |
| 10,406,123 B2 | 9/2019 | Golan | | |
| 2010/0113512 A1 | 5/2010 | Ignar | | |
| 2011/0046236 A1 * | 2/2011 | Czarnik | ................ | A61K 9/0095 |
| | | | | 426/11 |
| 2012/0122823 A1 * | 5/2012 | Reed | ................ | A61K 47/6951 |
| | | | | 514/165 |
| 2018/0085326 A1 | 3/2018 | Golan | | |
| 2019/0054042 A1 | 2/2019 | Golan | | |
| 2020/0000747 A1 | 1/2020 | Golan | | |

FOREIGN PATENT DOCUMENTS

| | | | |
|---|---|---|---|
| DE | 952441 C | * | 11/1956 |
| EP | 2556830 | | 2/2013 |
| WO | WO 95/04713 | | 2/1995 |
| WO | WO 99/14207 | | 3/1999 |
| WO | WO 99/19325 | | 4/1999 |
| WO | WO 01/34172 | | 5/2001 |
| WO | WO 02/064545 | | 8/2002 |
| WO | WO 2004/037777 | | 5/2004 |
| WO | WO 2006/015828 | | 2/2006 |
| WO | WO 2007/069925 | | 6/2007 |

(Continued)

OTHER PUBLICATIONS

Brandt, S.D., Braithwaite, R.A., Evans-Brown, M., Kiernan, A.T. 2013. "Aminoindane Analogues." Novel Psychoactive Substances. Elsevier, pp. 261-283.*
International Preliminary Report on Patentability dated Jun. 22, 2017 From the International Bureau of WIPO Re. Application No. PCT/IL2015/051193. (8 Pages).
International Preliminary Report on Patentability dated Jun. 22, 2017 From the International Bureau of WIPO Re. Application No. PCT/IL2015/051194. (8 Pages).

(Continued)

*Primary Examiner* — Nikki H. Dees

(74) *Attorney, Agent, or Firm* — Finnegan, Henderson, Farabow, Garrett & Dunner, LLP

(57) ABSTRACT

Alcoholic beverage-substitutes such as a beer-substitute, a wine-substitute, a cider-substitute, an alcopop-substitute or a spirit-substitute beverage, comprising a base liquid (e.g., a base beverage) and a 2-aminoindan derivative such as defined by Formula I in the specification are disclosed.

11 Claims, No Drawings

(56) References Cited

FOREIGN PATENT DOCUMENTS

| WO | WO 2009/125923 | 10/2009 |
|---|---|---|
| WO | WO 2016/092546 | 6/2016 |
| WO | WO 2016/092547 | 6/2016 |

OTHER PUBLICATIONS

International Search Report and the Written Opinion dated Apr. 4, 2016 From the International Searching Authority Re. Application No. PCT/IL2015/051193.
International Search Report and the Written Opinion dated Mar. 22, 2016 From the International Searching Authority Re. Application No. PCT/IL2015/051194.
Anton et al. "Combined Pharmacotherapies and Behavioral Interventions for Alcohol Dependence", Journal of the American Medical Association, JAMA, 295(17): 2003-2017, May 3, 2006.
Bluelight "5-Meo-AI", Bluelight, 6 P., Dec. 31, 2014.
Boyce et al. "Enhancement of Ethanol Reward By Dopamine D3 Receptor Blockade", Brnn Rasearch, 88(1): 202-206, Aug. 2, 2000.
Burn-Callander et al. "Get Drunk Without a Hangover on Synthetic Booze", Telegraph Media Group, 4 P., Jan. 22, 2015.
Chick et al. "Substitution Therapy for Alcoholism: Time for a Reappraisal?", Journal of Psychopharmacology, 26(2): 205-212, Published Online Jul. 8, 2011.
Fisher "Doctors Have Discovered the Simplest Way to Quit Drinking—By Doing Drugs", Mic, 2 P., Jan. 8, 2015.
Gray "Could a Legal High That Mimics Ecstasy Stop People From Boozing? Party Drug Is Patented for Use as 'Binge Mitigation Agent'", Daily Mail Online, 16 P., Dec. 31, 2014.
Heidbreder et al. "Role of Dopamine D3 Receptors in the Addictive Properties of Ethanol", Drugs of Today, 40(4): 355-365, 2004.
Johnson "Progress in the Development of Topiramate for Treating Alcohol Dependence: From a Hypthesis to a Proof-of-Concept Study", Alcoholism: Clinical and Experimental Research, 28(8): 1137-1144, Aug. 2004.
Karhuvaara et al. "Targeted Nalmefene With Simple Medical Management in the Treatment of Heavy Drinkers: A Randomized Double-Blind Placebo-Controlled Multicenter Study", Alcolholism: Clinical and Experimental Research, 31(7): 1179-1187, Jul. 2007.
Koob "Alcoholism: Allostasis and Beyond", Alcoholism: Clinical and Experimental Research, 27(2): 232-243, Feb. 2003.
Lingford-Hughes et al. "Neuropharmacology of Addiction and How It Informs Treatment", British Medical Bulletin, 96: 93-110, Published Online Nov. 2, 2010.
Nutt "Alcohol Without the Hangover? It's Closer Than You Think ", The Guardian, 2 P., Nov. 11, 2013.
Nutt et al. "Through a Glass Darkly: Can We Improve Clarity About Mechanism and Aims of Medications in Drug and Alcohol Treatments?", Journal of Physchopharmacology, 26(2): 199-204, Feb. 2012.
Roesner et al. "Acamprosate Supports Abstinence, Naltrexone Prevents Excessive Drinking: Evidence From a Meta-Analysis With Unreported Outcomes", Journal of Psychopharmacology, 22(1): 11-23, Jan. 2008.
Skett "Care for a Legal Hight That's 'Chaperon-ed by Imperial'? New Party Drug Currently Being Developed by Nutt's Team Could Stop Binge Drinking But Still Deliver a High", News—Felix Online, 5 P., Jan. 16, 2015.
Slezak "High and Dry? Patty Drug Could Target Excess Drinking. A Patent Has Been Filed for a Drug That Produces Some of Ecstasy's Euphoric Effects—and Seems to Put the Brakes on Boozing", New Scientist, 5 P., Dec. 30, 2014.
Traits "How Safe Are My Drugs?", BBC Three, 3 P., Jan. 29, 2015.
Vengeliene et al. "The Dopamine D3 Receptor Plays an Essential Role in Alcohol-Seeking and Relapse", The FASEB Journal, 20(13): 2223-2233, Jan. 1, 2006.
Weiss et al. "Behavioral Neurobiology of Alcohol Addiction: Recent Advances and Challenges", The Journal of Neuroscience, 22(9): 3332-3337, May 1, 2002.
Wikipedia "MEAI", Wikipedia, the Free Encyclopedia, 2 P., Last Modified Dec. 13, 2015.
Official Action dated Mar. 14, 2018 From the US Patent and Trademark Office Re. U.S. Appl. No. 15/534,137. (13 pages).
Supplementary European Search Report and the European Search Opinion dated Jul. 2, 2018 From the European Patent Office Re. Application No. 15867070.3. (11 Pages).
Supplementary European Search Report and the European Search Opinion dated Jul. 2, 2018 From the European Patent Office Re. Application No. 15867972.0. (8 Pages).
Americ et al. "Potent Anorexic-like Effects of RDS-127 (2-di-n-propylamino-4, 7-dimethoxyindane) in the Rat: A Comparison with Other Dopamine-receptor Agonists", Neuropharmacology, XP025559703, 21(9), 885-890, Sep. 1, 1982.
Giuliano et al. "Attenuation of Cocaine and Heroin Seeking by [mu]-opioid Receptor Antagonism", Psychopharmacology, XP035370001, 227(1): 137-147, Published Online Jan. 9, 2013.
Kelly et al. "The Opioid Receptor Pharmacology of GSK1521498 Compared to Other Ligands With Differential Effects on Compulsive Reward-related Behaviours", Psychopharmacology, XP035416399, 232(1): 305-314, Published Online Jun. 29, 2014.
Ziauddeen et al. "Effects of the Mu-opioid Receptor Antagonist GSK1521498 on Hedonic and Consummatory Eating Behaviour: A Proof of Mechanism Study in Binge-Eating Obese Subjects", Molecular Psychiatry, XP9506312, 18(12): 1287-1293, Published Online Nov. 13, 2012. p. 1288, col. 2, Para [0001], p. 1292.
Notification of Office Action and Search Report dated Dec. 20, 2018 From the State Intellectual Property Office of the People's Republic of China Re. Application No. 201580075677.4 and Its Summary in English. (12 Pages).
Notification of Office Action and Search Report dated Dec. 20, 2018 From the State Intellectual Property Office of the People's Republic of China Re. Application No. 201580075683.X and Its Summary in English. (13 Pages).
Akincioglu et al. "Novel Sulfamides as Potential Carbonic Anhydrase Isoenzymes Inhibitors", Bioorganic & Medicinal Chemistry, 21(6): 1379-1385, Available Online Jan. 22, 2013.
Haadsma-Svensson et al. "Dopamine D3 Receptor Antagonists.1. Synthesis and Structure-Activity Relationships of 5,6-Dimethoxy-N-Alkyl- and N-Alkylaryl-Substituted 2-Aminoindans", The Journal of Medicinal Chemistry, 44(26): 4716-4732, Published on Web Nov. 17, 2001.
Official Action dated Dec. 11, 2018 From the US Patent and Trademark Office Re. U.S. Appl. No. 16/167,576. (13 pages).
Notification of Office Action dated Aug. 21, 2019 From the National Intellectual Property Administration of the People's Republic of China Re. Application No. 201580075677.4 and Its Translation Into English. (17 Pages).
Notification of Office Action dated Aug. 21, 2019 From the National Intellectual Property Administration of the People's Republic of China Re. Application No. 201580075683.X and Its Translation Into English. (15 Pages).
Examination Report Under Sections 12 & 13 of the Patents Act, 1970 and the Patents Rules, 2003 dated Dec. 24, 2019 From the Government of India, Intellectual Property India, Patents. Designs, Trade Marks, Geographical Indications, The Patent Office Re. Application No. 201727023745. (7 Pages).
Examination Report Under Sections 12 & 13 of the Patents Act, 1970 and the Patents Rules, 2003 dated Nov. 7, 2019 From the Government of India, The Patent Office, Intellectual Property India, Patents, Designs, Trade Marks, Geographical Indications Re. Application No. 201727023744. (6 Pages).
Official Action dated Oct. 3, 2019 From the US Patent and Trademark Office Re. U.S. Appl. No. 16/563,974. (15 pages).
European Search Report and the European Search Opinion dated Aug. 12, 2020 From the European Patent Office Re. Application No. 20161755.2. (14 Pages).
Akbaba et al. "Synthesis and Asymmetric Resolution of a Dopaminergic Compound: 2-Amino-5-Methoxyindane", Tetrahedron Asymmetry, XP029554246, 27(11): 475-479, Available Online Apr. 28, 2016.

(56) References Cited

OTHER PUBLICATIONS

Shimshoni et al. "Toxicological Evaluation of 5-Methoxy-2-Aminoindane (MEAI): Binge Mitigating Agent in Development", Toxicology and Applied Pharmacology, XP029927268, 319: 59-68, Available Online Feb. 4, 2017.
Decision on Rejection dated Mar. 26, 2020 From the National Intellectual Property Administration of the People's Republic of China Re. Application No. 201580075683.X and Its Translation Into English. (14 Pages).
Decision on Rejection dated Mar. 26, 2020 From the National Intellectual Property Administration of the People's Republic of China Re. Application No. 201580075683.X and Its Translation Into English. (24 Pages).
Final Official Action dated Jun. 10, 2020 from the US Patent and Trademark Office Re. U.S. Appl. No. 16/563,974. (10 pages).
Examination Report Under Sections 12 & 13 of the Patents Act, 1970 and the Patents Rules, 2003 dated Nov. 7, 2020 From the Government of India, The Patent Office, Intellectual Property India, Patents, Designs, Trade Marks, Geographical Indications Re. Application No. 201727023744. (6 Pages).

\* cited by examiner

ALCOHOLIC BEVERAGE SUBSTITUTES

RELATED APPLICATIONS

This application is a National Phase of PCT Patent Application No. PCT/IL2015/051194 having International filing date of Dec. 9, 2015, which claims the benefit of priority under 35 USC § 119(e) of U.S. Provisional Patent Application Nos. 62/089,504 and 62/089,500, both filed on Dec. 9, 2014. The contents of the above applications are all incorporated by reference as if fully set forth herein in their entirety.

FIELD AND BACKGROUND OF THE INVENTION

The present invention, in some embodiments thereof, relates to alcoholic beverage substitutes.

Alcohol consumption presents a growing problem worldwide, which some believe may have already overtaken tobacco in terms of overall health and social care costs. Excessive and/or prolonged alcohol consumption may have some undesired physiological and psychological including short-term effects such as gastric irritation, anxiety disorders and other excitable states, and longer-term effects such as cirrhosis, cardiomyopathy and dementia. Alcohol consumption may lead to intoxication, which, in turn, can have serious consequences such as accidents and uncontrolled violent behavior with subsequent medical complications.

The toxic element in alcohol is ethanol, a two-carbon chain alcohol that has a complex pharmacology. The sedative, ataxic and eventually terminal anaesthetic actions of ethanol are thought to be mediated by interactions with primary amino acid ionotropic receptors, especially $GABA_A$ and glutamate. Ethanol is known to act as a $GABA_A$ agonist, and hence increases inhibition of central GABA receptors, and as antagonist of the NMDA type of glutamate receptors, and hence reduces excitation in the central nervous system. The pleasurable effects associated with alcohol consumption are attributed, at least in part, to these interactions, but are assumed to also involve interactions with endogenous opioids, dopamine and other amine systems. Aspects of alcohol toxicity may reflect specific interactions, e.g., the nausea is in part due to agonist actions at the 5HT3 receptor leading to vagal nerve stimulation.

The standard way alcohol is consumed is by drinking, usually over a few hours. In the case of beers/lagers, alcohol is provided as relatively dilute solution, wines are stronger and spirits contain the maximum alcohol concentration that can be obtained by simple distillation.

One major reason for the increase in binge intoxication is the gradual increase in the strength of alcohol in beers and especially lagers. Thirty years ago the average strength of beers and lagers was between 3.5 and 4%. Now a days, such weak drinks are almost not sold in bars, as the most popular drinks are in the 5-5.5% range and some strong lagers are up to 8% alcohol.

One approach to reduce or abolish the undesired effects of ethanol is to reduce the concentration of alcohol in drinks. Dealcoholized beverages have been known for nearly 100 years. For example, U.S. Pat. No. 1,390,710 discloses carbonated or effervescent low alcoholic beverages, more specifically a beer selected from ale, stout, porter, and the like, said to have the taste, flavor, body and other beverage characteristics of fermented alcoholic beer, obtained by boiling the beer in the open air or in vacuum until substantially all of the alcohol has been eliminated. U.S. Pat. Nos. 1,256,894, 6,472,009, 1,401,700, 4,999,209, and 4,612,916 and UK Patent Application GB 2,133,418 also teach various methods for removing alcohol from alcoholic drinks.

While removing alcohol may seem a practical option for beers/lagers, in some cases, especially in wine and spirits, there is a marked deterioration in taste as well. No matter what precautions are taken in effecting the removal of the alcohol by boiling or steaming, there is invariably a deleterious effect produced upon the flavor, taste, bouquet, and other qualities of the beverage, which are the criteria of its beverage character. The cause of this deleterious effect has been attributed to removal of the volatile alcohols and volatile esters, to caramelization of carbohydrates, to coagulation or other injurious or destructive action upon the nitrogenous constituents of the beverage base, and to numerous other causes. In order to restore to the dealcoholized beverage its original flavor, taste, etc., or to produce desired fermentation flavors and tastes therein, several expedients have been proposed, such as carrying out the dealcoholization under high vacuum and returning to the dealcoholized beverage some higher alcohols and esters.

Another approach which has been practiced is the "safer alcohol" approach, which utilizes drugs that act in a similar way to alcohol but are free of some of its immediate adverse effects, such as, for example, gastric irritation, and do not produce the longer-term effects such as cirrhosis, cardiomyopathy and dementia. The three main drug alternatives to alcohol that have been applied for alcohol withdrawal and treatment of anxiety disorders and other excitable states associated with excessive alcohol consumption include (i) Clomethiazole, a sedative hypnotic drug that was developed for sleep induction; (ii) benzodiazepine; and (iii) gamma-hydroxybutyrate (GHB), also used as an anaesthetic agent. All these drugs had limited use as treatment alternatives due to development of dependence thereon, and/or abuse thereof, and further since drinking alcohol on top of each of them could lead to excessive sedation and intoxication and potentially terminal coma.

Current efforts are directed towards finding agents that counteract one or more of ethanol's pharmacological effects as treatments for alcohol abuse and dependence, or developing other drugs whose actions are not reinforced by alcohol.

As indicated hereinabove, $GABA_A$ receptor is one of the preferred receptor targets for an alcohol substitute. Many $GABA_A$ receptor subunits ($\alpha_1$, $\alpha_2$, $\beta_2$, $\beta_3$, $\gamma_2$ and $\delta$) have been shown to be involved in one or more aspects of ethanol behavioural sensitivity. Several studies have been conducted for understanding the $GABA_A$ benzodiazepine receptor (see, for example, Nutt and Malizia, 2001), and partial agonists of the $GABA_A$ receptor benzodiazepine site (abbreviated herein as PAs) have been synthesized, and some tested in humans as potential anxiolytics (Potokar and Nutt, 1994). PAs such as bretazenil show little sedation even in overdose, and few signs of dependence or withdrawal in animals have been reported. Moreover, they seem to have low to zero abuse propensity and have the additional safety benefit over alcohol, that an overdose can be instantly reversed by administering an antagonist such as, for example, flumazenil.

However, though seemingly attractive particularly due to an assumed ability to avoid the problems of tolerance, dependence and withdrawal, and be safer in that their pharmacological actions would not increase with higher dose, these effects of PAs have never been substantiated clinically. Moreover, it has been known that the $GABA_A$ receptors are not the sole pharmacological targets of alcohol.

For example, and as indicated hereinabove, alcohol is an NMDA receptor antagonist (Woodward, 2000). While drugs that act as G-protein coupled glutamate receptors or as NMDA antagonist have been developed, it is not clear yet whether NMDA receptors are responsible for the attractive features of alcohol or the unpleasant ones. Sedative effects may also be mediated, inter alia, by certain isoforms of calcium-stimulated adenylyl cyclase (Mass et al., 2005).

The dopamine D3 receptor subtype is a known target of anti-psychotics, and shows a high abundance in brain regions associated with emotional and cognitive functions. Compounds derived from 2-aminoindan have been shown to selectively bind to the dopamine D3 receptor. U.S. Pat. No. 5,708,018 discloses some 2-aminoindan derivatives, and hypothesizes that these 2-aminoindan derivatives may be useful in treating CNS disorders associated with dopamine D3 receptor, such as mania, depression, drug abuse and addiction, anxiety disorders, and sleep disorders.

SUMMARY OF THE INVENTION

There is an unmet need for "safer" alcoholic drinks that would not deprive the drinker from the pleasure and psychotropic effects provided by drinking alcoholic beverage, yet, would reduce or be devoid of the adverse effects associated with alcohol consumption.

The present invention discloses alcoholic beverage substitutes, comprising a derivative of 2-aminoindan, as described herein.

The alcoholic beverage substitutes disclosed herein impart features such as psychotropic effect, palatability and pleasure that are attributed to alcoholic beverage, while avoiding the harmful effects associated with alcohol consumption. The 2-aminoindan derivatives utilized in embodiments of the present invention are characterized as:

(i) being intoxicating in a way similar to alcohol;
(ii) being physiologically benign (namely, non harmful); and
(iii) being devoid of interactions with other drugs.

According to an aspect of some embodiments of the present invention there is provided an alcoholic beverage-substitute comprising a base liquid and a compound represented by Formula I:

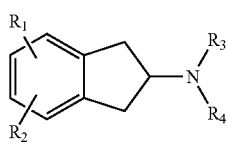

Formula I wherein:

each of $R_1$ and $R_2$ is independently selected from the group consisting of H, $(C_1\text{-}C_8)$alkyl, $(C_2\text{-}C_8)$alkenyl, $(C_2\text{-}C_8)$alkynyl, $(C_3\text{-}C_8)$cycloalkyl, aryl, heteroaryl, heteroalicyclic, —O$(C_1\text{-}C_8)$alkyl, OH, —OSO$_2$CF$_3$, —OSO$_2$—$(C_1\text{-}C_8)$alkyl, —SOR$_5$, —CO$_2$R$_5$, —CONR$_5$R$_6$, —COR$_5$, —CF$_3$, CN, —SR$_5$, —SO$_2$NR$_5$R$_6$, —SO$_2$R$_5$, —OCO—$(C_1\text{-}C_8)$alkyl, —NCO—$(C_1\text{-}C_8)$alkyl, —CH$_2$O—$(C_1\text{-}C_8)$alkyl, —$(C_1\text{-}C_6)$alkyl-OH, —NHSO$_2$R$_5$, and halogen, or, alternatively, $R_1$ and $R_2$ together with two or more of the phenyl carbon atoms form a —X$_1$—(CR$_5$R$_6$)$_m$—X$_2$— ring, wherein each of X$_1$ and X$_2$ is independently selected from C, O, NH or S and m is 1, 2, 3, or 4;

each of $R_3$ and $R_4$ is independently selected from the group consisting of H, $(C_1\text{-}C_8)$alkyl, $(C_2\text{-}C_8)$alkenyl, $(C_2\text{-}C_8)$alkynyl, $(C_3\text{-}C_8)$ cycloalkyl, and —(CH$_2$)$_p$-thienyl, wherein p is 1, 2, 3, or 4, or alternatively, $R_3$ and $R_4$ are joined together to form a heterocylic ring (heteroalicyclic or heteroaryl) containing the nitrogen atom to which they are attached; and each of $R_5$ and $R_6$ is independently selected from the group consisting of H, $(C_1\text{-}C_8)$alkyl, $(C_2\text{-}C_8)$alkenyl, $(C_3\text{-}C_8)$cycloalkyl and aryl;

or a physiologically acceptable salt thereof.

According to some of any of the embodiments of the present invention, each of $R_1$ and $R_2$ is independently selected from the group consisting of H, $(C_1\text{-}C_8)$alkyl, $(C_2\text{-}C_8)$alkenyl, $(C_2\text{-}C_8)$alkynyl, $(C_3\text{-}C_8)$cycloalkyl, aryl, —OCH$_3$, OH, —OSO$_2$CF$_3$, —OSO$_2$CH$_3$, —SOR$_5$, —CO$_2$R$_5$, —CONR$_5$R$_6$, —COR$_5$, —CF$_3$, —CN, —SR$_5$, —SO$_2$NR$_5$R$_6$, —SO$_2$R$_5$, —CH$_2$—OH, halogen, phthalimidyl, thiophenyl, pyrrolyl, pyrrolinyl, and oxazolyl, or, alternatively, $R_1$ and $R_2$ together with two or more of the phenyl carbon atoms form a —O(CH$_2$)$_m$O— ring, wherein m is 1 or 2;

$R_3$ and $R_4$ are joined together to form a heterocylic ring containing 4 to 8 carbon atoms with the nitrogen atom to which they are attached; and each of $R_5$ and $R_6$ is independently selected from the group consisting of H, $(C_1\text{-}C_8)$ alkyl, $(C_2\text{-}C_8)$ alkenyl, and $(C_3\text{-}C_8)$ cycloalkyl.

According to some of any of the embodiments of the present invention, at least one of $R_3$ and $R_4$ is H.

According to some of any of the embodiments of the present invention, each of $R_1$ and $R_2$ is H, —OCH$_3$, or —OSO$_2$CF$_3$, or $R_1$ and $R_2$ together with two or more of the phenyl carbon atom form a —O(CH$_2$)$_m$O— ring, wherein m is 1 or 2.

According to some of any of the embodiments of the present invention, $R_3$ or $R_4$ is propyl.

According to some of any of the embodiments of the present invention, the compound is selected from:

5-methoxy-2-aminoindan;
5,6-dimethoxy-2-aminoindan;
5-methoxy-2-(N-propylamino)indan;
5,6-dimethoxy-2-(N-propylamino)indan;
5,6-dimethoxy-2-(di-N-butylamino)indan;
5-(trifluoromethylsulfonyloxy)-2-(N-propylamino)indan;
5,6-(di-trifluoromethylsulfonyloxy)-2-(N-propylamino) Indan;
5,6-dimethoxy-2(pyrrolidino)indan;
5-(trifluoromethylsulfonyloxy)-6-hydroxy-2-(di-N-propylamino)indan;
5-(trifluoromethylsulfonyloxy)-6-acetoxy-2-(di-N-propylamino)indan;
5-trifluromethansulfonyloxy-6-methoxy-2-(di-N-propylamino)indan;
5,6-ethylenedioxy-2-(di-N-propylamino)indan; and
5,6-methylenedioxy-2-(di-N-propylamino)indan.

According to some of any of the embodiments of the present invention, the base liquid is a beverage selected from fruit juice, fruit syrup, concentrate or nectar from fruits jello, vegetable juice, a plant material such as agave, a carbonated beverage such as cola, a caffeinated beverage, a specialized flavor formulation emulating the taste of existing wines and spirits, a non-alcoholic cocktail ("mocktails"), malt beer, a dealcoholized cider, a dealcoholized wine, a dealcoholized beer, a dealcoholized spirit, tonic water and water.

According to some of any of the embodiments of the present invention, the alcoholic beverage-substitute according is selected from a beer-substitute, a wine-substitute, a cider-substitute, a spirit-substitute and alcopop substitute beverage.

According to some of any of the embodiments of the present invention, the alcoholic beverage is a beer-substitute.

According to some of any of the embodiments of the present invention, the beer-substitute is selected from an ale-substitute, a stout-substitute, a porter-substitute, and a lager-substitute.

According to some of any of the embodiments of the present invention, the beer-substitute comprises the compound represented by Formula I in an amount that imparts to the beverage the psychotropic effect, palatability and the pleasures of drinking provided by an alcoholic beer containing 4.8-10% alcohol by volume.

According to some of any of the embodiments of the present invention, the beer-substitute comprises the compound represented by Formula I in an amount within a range selected from 0.20 mg/ml to 0.70 mg/ml, 0.20 to 0.68 mg/ml, 0.25 to 0.68 mg/ml, 0.28 to 0.66 mg/l, 0.30 to 0.66 mg/ml, 0.28 to 0.65 mg/ml, 0.28 to 0.60 mg/ml 0.30 to 0.60 mg/ml, 0.30 to 0.58 mg/ml, 0.30 to 0.55 mg/ml, 0.30 to 0.50 mg/ml, 0.30 to 0.48 mg/ml, 0.30 to 0.45 mg/ml, 0.30 to 0.42 mg/ml, 0.30 to 0.40 mg/ml, 0.30 to 0.38 mg/ml or 0.31 to 0.36 mg/ml.

According to some of any of the embodiments of the present invention, the beer-substitute comprises 0.31 mg/ml to 0.33 mg/ml of the compound.

According to some of any of the embodiments of the present invention, the beer-substitute comprises ethanol in an amount that is more than 0.01% by volume but less than 0.50%, less than 0.25%, less than 0.2%, less than 0.15%, less than 0.10%, or less than 0.05% by volume.

According to some of any of the embodiments of the present invention, the alcoholic beverage-substitute is a wine-substitute.

According to some of any of the embodiments of the present invention, the wine-substitute is selected from a dry red wine-substitute, a dry white wine-substitute, a semi-dry red wine-substitute, a semi-dry white wine-substitute, a rose wine-substitute, a dessert wine-substitute, a Port wine-substitute, a Champagne-substitute, a sparkling wine-substitute and vermouth-substitute.

According to some of any of the embodiments of the present invention, the alcoholic beverage-substitute comprises the compound represented by Formula I in amount that imparts to the beverage the psychotropic effect, palatability and the pleasures of drinking provided by an alcoholic wine containing 10-14% alcohol by volume.

According to some of any of the embodiments of the present invention, the alcoholic beverage-substitute beverage comprises the compound represented by Formula I in an amount within a range selected from 0.50 mg/ml to 1.25 mg/ml, 0.55 to 1.25 mg/ml, 0.55 to 1.20 mg/ml, 0.60 to 1.20 mg/l, 0.65 to 1.20 mg/ml, 0.70 to 1.20 mg/ml, 0.70 to 1.10 mg/ml, 0.75 to 1.10 mg/ml, 0.75 to 1.00 mg/ml, 0.78 to 1.00 mg/ml, 0.80 to 1.00 mg/ml, 0.80 to 1.05 mg/ml, 0.80 to 0.98 mg/ml or 0.80 to 0.95 mg/ml.

According to some of any of the embodiments of the present invention, the alcoholic beverage-substitute beverage comprises 0.79 mg/ml to 0.95 mg/ml of the compound.

According to some of any of the embodiments of the present invention, the wine-substitute comprises ethanol in an amount that is more than 0.01% by volume but less than 5.0%, less than 4.0%, less than 3.0%, less than 2.5%, less than 2.0%, less than 1.5%, less than 1.0%, less than 0.5%, less than 0.25%, less than 0.2%, less than 0.15%, less than 0.10%, or less than 0.05% by volume.

According to some of any of the embodiments of the present invention, the alcoholic beverage substitute is a spirit-substitute.

According to some of any of the embodiments of the present invention, the spirit-substitute is selected from a brandy-substitute, a liquor-substitute, saki-substitute, Ouzo-substitute, an arrack-substitute, a rum-substitute, a vodka-substitute, a tequila-substitute, a schnapps-substitute, a whiskey-substitute, a gin-substitute, a cordial-substitute, Cachaça-substitute and a slivovitz-substitute.

According to some of any of the embodiments of the present invention, the alcoholic beverage-substitute comprises the compound represented by Formula I in amount that imparts to the beverage the psychotropic effect, palatability and the pleasures of drinking provided by an alcoholic spirit containing 30-40% alcohol by volume.

According to some of any of the embodiments of the present invention, the alcoholic beverage-substituted beverage comprises the compound represented by Formula I in an amount within a range selected from 1.90 mg/ml to 2.97 mg/ml, 1.90 mg/ml to 2.64 mg/ml 1.90 mg/ml to 2.60 mg/ml, 1.90 to 2.55 mg/ml, 1.95 to 2.55 mg/ml, 1.95 to 2.50 mg/ml, 1.95 to 2.40 mg/ml, 1.95 to 2.30 mg/ml, 1.96 to 2.35 mg/l, 1.96 to 2.30 mg/ml, 1.96 to 2.28 mg/ml, 1.96 to 2.25 mg/ml, 1.96 to 2.20 mg/ml, 1.98 to 2.28 mg/ml, 1.98 to 2.25 mg/ml, or 1.98 to 2.20 mg/ml.

According to some of any of the embodiments of the present invention, the alcoholic beverage-substituted comprises 1.98 mg/ml to 2.20 mg/ml of the compound.

According to some of any of the embodiments of the present invention, the spirit-substitute comprises ethanol in an amount that is more than 0.01% but less than 15%, less than 14%, less than 12%, less than 11.0%, less than 10.0%, less than 9.0%, less than 8.0%, less than 7.0%, less than 6.0%, less than 4.50%, less than 4.00%, less than 3.50%, less than 3.00%, less than 2.50%, less than 2.00%, less than 1.50%, less than 1.00%, less than 0.50%, less than 0.25%, less than 0.2%, less than 0.15%, or less than 0.10%, by volume.

According to some of any of the embodiments of the present invention, the alcoholic beverage substitute is an alcopop-substitute.

According to some of any of the embodiments of the present invention, the alcopop-substitute is selected from a beer cooler, a wine cooler and a spirit cooler.

According to some of any of the embodiments of the present invention, the alcoholic beverage-substitute comprises the compound represented by Formula I in amount that imparts to the beverage the psychotropic effect, palatability and the pleasures of drinking provided by an alcopop beverage containing 4.5-12.5% alcohol by volume.

According to some of any of the embodiments of the present invention, the alcoholic beverage-substituted beverage comprises the compound represented by Formula I in an amount within a range selected from 0.25 to 0.60 mg/ml, 0.28 to 0.60 mg/l, 0.30 to 0.60 mg/ml, 0.28 to 0.58 mg/ml, 0.28 to 0.55 mg/ml 0.30 to 0.55 mg/ml, 0.30 to 0.50 mg/ml, 0.30 to 0.48 mg/ml, 0.30 to 0.45 mg/ml, 0.30 to 0.42 mg/ml, 0.30 to 0.40 mg/ml, 0.30 to 0.38 mg/ml or 0.31 to 0.36 mg/ml.

According to some of any of the embodiments of the present invention, the alcoholic beverage-substituted comprises 0.31 mg/ml to 0.33 mg/ml of the compound.

According to some of any of the embodiments of the present invention, the alcopop-substitute comprises ethanol in an amount that is more than 0.01% but less than 1.00%, less than 0.70%, less than 0.50%, less than 0.25%, less than 0.2%, less than 0.15%, less than 0.10%, or less than 0.05%, by volume.

According to an aspect of some embodiments of the present invention there is provided a beer beverage comprising the beer substitute beverage as described herein and ethanol in an amount that is more than 0.5% but less than 5.00%, less than 4.50%, less than 4.00%, less than 3.50%, less than 3.00%, less than 2.50%, less than 2.00%, less than 1.50%, or less than 1.00%, by volume.

According to an aspect of some embodiments of the present invention there is provided a wine beverage comprising the wine substitute beverage as described herein and ethanol in an amount that is more than 3.0% but less than 7.5%, less than 7.0%, less than 6.5%, less than 6.0%, less than 5.0%, less than 5.5%, less than 5.0%, less than 4.5%, less than 4.0%, or less than 3.5%, by volume.

According to an aspect of some embodiments of the present invention there is provided a spirit beverage comprising the spirit substitute beverage as described herein and ethanol in an amount that is more than 11.0% but less than 20.0%, less than 18.0%, less than 16.0%, less than 14.0%, less than 15.0%, less than 14.0%, less than 13.5%, less than 13.0%, less than 12.5%, or less than 12.0%, by volume.

According to an aspect of some embodiments of the present invention there is provided as alcopop beverage comprising the alcopop substitute beverage as described herein and ethanol in an amount that is more than 0.5% but less than 5.00%, less than 4.50%, less than 4.00%, less than 3.50%, less than 3.00%, less than 2.50%, less than 2.00%, less than 1.50%, or less than 1.00%, by volume.

According to an aspect of some embodiments of the present invention there is provided a beverage comprising an alcohol-free base liquid and a compound represented by Formula I as defined herein in an amount that imparts to the beverage the psychotropic effect, palatability and the pleasures of drinking provided by an alcoholic beverage having alcohol in an amount of 2% to 30% by volume.

According to some of any of the embodiments of the present invention, the amount of the compound represented by Formula I is in the rage selected from 0.20 mg/ml to 2.97 mg/ml, 0.20 mg/ml to 0.70 mg/ml, 0.28 to 0.65 mg/ml, 0.30 to 0.60 mg/ml, 0.30 to 0.55 mg/ml, 0.30 to 0.50 mg/ml, 0.30 to 0.45 mg/ml, 0.30 to 0.40 mg/ml, 0.31 to 0.36 mg/ml, 0.50 to 1.25 mg/ml, 0.55 to 1.20 mg/ml, 0.60 to 1.20 mg/ml, 0.70 to 1.20 mg/ml, 0.70 to 1.10 mg/ml, 0.75 to 1.00 mg/ml, 0.80 to 1.00 mg/ml, 0.80 to 1.05 mg/ml, 0.80 to 0.95 mg/ml, 1.25 to 1.90 mg/ml, 1.25 to 2.00 mg/ml, 1.90 to 2.97 mg/ml, 1.90 mg/ml to 2.60 mg/ml, 1.95 to 2.55 mg/ml, 1.95 to 2.50 mg/ml, 1.95 to 2.40 mg/ml, 1.96 to 2.30 mg/ml, 1.96 to 2.25 mg/ml, 1.96 to 2.20 mg/ml, 1.98 to 2.25 mg/ml, or 1.98 to 2.20 mg/ml.

According to some of any of the embodiments of the present invention, the beverage is selected from fruit juice, fruit syrup, concentrate or nectar from fruits, jello, vegetable juice, a plant material such as agave, a carbonated beverage such as cola, a caffeinated beverage, malt beer, tonic water and water.

According to an aspect of some embodiments of the present invention there is provided a compound represented by Formula I, as described herein in any one of the respective embodiments, for use in the manufacture of an alcoholic beverage substitute, or an alcoholic-like beverage.

According to an aspect of some embodiments of the present invention there is provided a use of a compound represented by Formula I, as described herein in any one of the respective embodiments, for the preparation of an alcoholic beverage-substitute, or an alcoholic-like beverage.

According to some of any of the embodiments of the present invention, alcoholic beverage substitute is selected from the group consisting of a beer-substitute, a wine-substitute, a spirit-substitute and an alcopop substitute.

According to an aspect of some embodiments of the present invention there is provided a process for the preparation of an alcoholic beverage substitute, the process comprising mixing a base liquid with a compound represented by Formula I in an amount that accounts for the psychotropic and palatability effects imparted by the alcoholic beverage.

According to some of any of the embodiments of the present invention, the amount of the compound represented by Formula I is in the range selected from 0.20 mg/ml to 2.97 mg/ml, 0.20 mg/ml to 0.70 mg/ml, 0.28 to 0.65 mg/ml, 0.30 to 0.60 mg/ml, 0.30 to 0.55 mg/ml, 0.30 to 0.50 mg/ml, 0.30 to 0.45 mg/ml, 0.30 to 0.40 mg/ml, 0.31 to 0.36 mg/ml, 0.50 to 1.25 mg/ml, 0.55 to 1.20 mg/ml, 0.60 to 1.20 mg/ml, 0.70 to 1.20 mg/ml, 0.70 to 1.10 mg/ml, 0.75 to 1.00 mg/ml, 0.80 to 1.00 mg/ml, 0.80 to 1.05 mg/ml, 0.80 to 0.95 mg/ml, 1.25 to 1.90 mg/ml, 1.25 to 2.00 mg/ml, 1.90 to 2.97 mg/ml, 1.90 mg/ml to 2.60 mg/ml, 1.95 to 2.55 mg/ml, 1.95 to 2.50 mg/ml, 1.95 to 2.40 mg/ml, 1.96 to 2.30 mg/ml, 1.96 to 2.25 mg/ml, 1.96 to 2.20 mg/ml, 1.98 to 2.25 mg/ml, or 1.98 to 2.20 mg/ml.

According to some of any of the embodiments of the present invention, the process further comprises adding to the base liquid at least one of a flavoring agent, a colorant, an odoriferous agent, $CO_2$, a viscosity modifying agent, a foaming agent, an antifoaming agent and a preservative.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DETAILED DESCRIPTION OF THE INVENTION

The present invention, in some embodiments thereof, relates to alcoholic beverage substitutes.

Before explaining at least one embodiment of the invention in detail, it is to be understood that the invention is not necessarily limited in its application to the details set forth in the following description.

Alcohol is one of the favorite, commonly used, yet most dangerous psychoactive substances. People drink alcohol for several reasons, which include quenching thirst, heating or cooling the drinker, for the taste and because of the association alcoholic drinks have with other aspects of life such as food and friendship. The psychotropic effects of alcohol contribute to some of these reasons.

Dealcoholized beer and wine are already available in reasonably palatable forms. However, while non-alcoholic drinks can fill such use-values of alcoholic beverages as quenching thirst and heating or cooling the drinker, they do not provide the range of psychoactivity and palatability which people are seeking from alcohol.

The mechanisms by which alcohol causes its effects are still not completely understood. While it is known with which receptors alcohol interacts, it is not known which of these interactions are responsible for the anxiolytic, sedative, motor, cognitive and/or addictive effects associated with alcohol consumption. Studies conducted thus far have shown the involvement of several CNS receptors in the effects associated with alcohol consumption, including $GABA_A$ receptors, NMDA receptors and calcium-stimulated adenylyl cyclase (AC).

However, it is highly unlikely that the cocktail bar of the future will offer the customer a subtype-specific $GABA_A$ agonist of one's choice, with a dash of NMDA antagonist, a calcium-stimulated AC stimulator and a cherry.

Part of the pleasure of alcohol—at least for the non-dependent drinker—is the taste and the associated rituals of consumption that may fill primitive appetitive functions. The standard way alcohol is consumed is by drinking, usually over a few hours. Thus, it has been contemplated by the present inventor that providing alcohol alternatives in a drinkable form that maintain the taste, palatability and psychotropic effect of alcohol, would not impair the pleasures associated with drinking an alcoholic beverage, yet would avoid the harmful effects thereof. Moreover, drinking allows the titration of input in a way that taking a pill does not.

Embodiments of the present invention therefore concern the provision of drinkable substances which provide the drinker with the palatability and psychotropic effect of alcohol, and which are devoid of the adverse effects associated with alcohol consumption. In some embodiments, the drinkable substances provided herein are referred to as alcoholic-beverage substitutes, which contain a reduced or even nullified amount of alcohol.

Embodiments of the present invention concern drinkable substances containing one or more aminoindan derivatives, and, more particularly, 2-aminoindan derivatives, collectively represented by Formula I as presented herein, which are mostly known as dopamine D2 and/or D3 receptor ligands. Mixing these compounds with liquid provides inebriating beverages that resemble, for example, beer or wine or a spirit in their user's experience. These beverages, although intoxicating in a way similar to alcohol (e.g., when consumed at low dosages) and even having some anxiolytic and sedative effects, are not harmful in terms of motor, cognitive and addictive effects attributed to consumption of alcoholic beverages. These beverages are therefore less toxic than commonly used ethanol-containing alcoholic beverages.

Exemplary embodiments of the present invention are of a beverage that is a beer substitute, obtained by mixing 125 mg of a 2-aminoindan derivative into 300 ml of a base liquid, and of a beverage that it a wine substitute, obtained by mixing this amount of the 2-aminoindan derivative into 120 ml of a base liquid.

According to an aspect of some embodiments of the present invention there is provided an alcoholic beverage-substitute comprising a base liquid and a compound represented by Formula I:

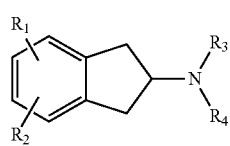

Formula I wherein:

each of $R_1$ and $R_2$ is independently selected from the group consisting of H, $(C_1-C_8)$alkyl, $(C_2-C_8)$alkenyl, $(C_2-C_8)$alkynyl, $(C_3-C_8)$cycloalkyl, aryl, heteroaryl, heteroalicyclic, —$O(C_1-C_8)$alkyl, OH, —$OSO_2CF_3$, —$OSO_2$—$(C_1-C_8)$alkyl, —$SOR_5$, —$CO_2R_5$, —$CONR_5R_6$, —$COR_5$, —$CF_3$, CN, —$SR_5$, —$SO_2NR_5R_6$, —$SO_2R_5$, —OCO—$(C_1-C_8)$alkyl, —NCO—$(C_1-C_8)$alkyl, —$CH_2O$—$(C_1-C_8)$alkyl, —$(C_1-C_6)$alkyl-OH, —$NHSO_2R_5$, and halogen, or, alternatively, $R_1$ and $R_2$ together with two or more of the phenyl carbon atoms form a —$X_1$—$(CR_5R_6)_m$—$X_2$— ring, wherein each of $X_1$ and $X_2$ is independently selected from C, O, NH or S and m is 1, 2, 3, or 4;

each of $R_3$ and $R_4$ is independently selected from the group consisting of H, $(C_1-C_8)$alkyl, $(C_2-C_8)$alkenyl, $(C_2-C_8)$alkynyl, $(C_3-C_8)$ cycloalkyl, and —$(CH_2)_p$-thienyl, wherein p is 1, 2, 3, or 4, or alternatively, $R_3$ and $R_4$ are joined together to form a heterocylic ring (heteroalicyclic or heteroaryl) containing the nitrogen atom to which they are attached; and each of $R_5$ and $R_6$ is independently selected from the group consisting of H, $(C_1-C_8)$alkyl, $(C_2-C_8)$alkenyl, $(C_3-C_8)$cycloalkyl and aryl.

In some embodiments of the invention, the alcoholic beverage-substitute comprises a 2-aminoindan derivative represented by Formula I as presented herein, wherein $R_1$-$R_6$ are defined as follows:

each of $R_1$ and $R_2$ is independently selected from the group consisting of H, $(C_1-C_8)$alkyl, $(C_2-C_8)$alkenyl, $(C_2-C_8)$alkynyl, $(C_3-C_8)$cycloalkyl, aryl, —$OCH_3$, OH, —$OSO_2CF_3$, —$OSO_2CH_3$, —$SOR_5$, —$CO_2R_5$, —$CONR_5R_6$, —$COR_5$, —$CF_3$, —CN, —$SR_5$, —$SO_2NR_5R_6$, —$SO_2R_5$, —$CH_2$—OH, halogen, phthalimidyl, thiophenyl, pyrrolyl, pyrrolinyl, and oxazolyl, or, alternatively, $R_1$ and $R_2$ together with two or more of the phenyl carbon atoms form a —$O(CH_2)_mO$— ring, wherein m is 1 or 2;

$R_3$ and $R_4$ are joined together to form a heterocylic ring containing 4 to 8 carbon atoms with the nitrogen atom to which they are attached; and each of $R_5$ and $R_6$ is independently selected from the group consisting of H, $(C_1-C_8)$ alkyl, $(C_2-C_8)$ alkenyl, and $(C_3-C_8)$ cycloalkyl.

In some embodiments, the alcoholic beverage-substitute of the invention comprises the compound represented by Formula I as described herein wherein the amino group is a secondary or tertiary amine, namely at least one of $R_3$ and $R_4$ is an alkyl, for example, propyl. Secondary (or tertiary) amino groups are preferred as the 2-aminoindan derivatives containing a secondary (or tertiary) amine moiety are less susceptible to enzymatic degradation by e.g., monoamine oxidase (MAO) enzymes and are thus more potent than primary amines when acting in the brain. In addition, secondary or tertiary amines are more hydrophobic and hence are more brain permeable.

In some embodiments, the alcoholic beverage-substitute comprises a compound represented by Formula I, as described herein, wherein $R_1$ and $R_2$ is each independently H, —$OCH_3$, or —$OSO_2CF_3$, or $R_1$ and $R_2$ together with two or more of the phenyl carbon atom form a —$O(CH_2)_mO$— ring, wherein m is 1 or 2.

Non-limiting examples of 2-aminoindan derivatives, which may be used for the preparation of the alcoholic beverage-substitutes described herein, include:

(1) 5-methoxy-2-aminoindan;
(2) 5,6-dimethoxy-2-aminoindan;
(3) 5-methoxy-2-(N-propylamino)indan;

(4) 5,6-dimethoxy-2-(N-propylamino)indan;
(5) 5,6-dimethoxy-2-(di-N-butylamino)indan;
(6) 5-(trifluoromethylsulfonyloxy)-6-hydroxy-2-(di-N-propylamino)indan;
(7) 5-(trifluoromethylsulfonyloxy)-2-(N-propylamino)indan;
(8) 5,6-(di-trifluoromethylsulfonyloxy)-2-(N-propylamino)indan;
(9) 5,6-dimethoxy-2(pyrrolidino)indan;
(10) 5-(trifluoromethylsulfonyloxy)-6-acetoxy-2-(di-N-propylamino)indan;
(11) 5-trifluromethansulfonyloxy-6-methoxy-2-(di-N-propylamino)indan;
(12) 5,6-ethylenedioxy-2-(di-N-propylamino)indan;
(13) 5,6-methylenedioxy-2-(di-N-propylamino)indan;
(14) 5-hydroxy-2-(n-propylamino)indan;
(15) 5,6-dihydroxy-2-(n-propylamino)indan;
(16) 4-methyl-2-aminoindan;
(17) 4,5-di-methyl-2-aminoindan;
(18) 5,6-di-methyl-2-aminoindan;
(19) 6-methyl-2-aminoindan;
(20) 4-fluoro-2-aminoindan;
(21) 5-(i-propyl)-2-aminoindan;
(22) 4,6-dimethyl-2-aminoindan;
(23) 4,7-dimethyl-2-aminoindan;
(24) 5-(t-butyl)-2-aminoindan;
(25) 5-propyl-2-aminoindan;
(26) 5-fluoro-2-(di-N-propylamino)indan;
(27) 6-methylenedioxy-2-(di-N-propylamino)indan;
(28) 5,6-dimethoxy-2(pyrrolidino)indan;
(29) 5,6-(di-carbomethoxy)-2-(di-N-propylamino)indan;
(30) 5-(carbomethoxy)-6-hydroxy-2-(di-N-propylamino)indan;
(31) 5-bromo-2-(dipropylamino)indan;
(32) (6-methylsulfanyl-indan-2-yl)-dipropyl-amine;
(33) (6-methylsulfonyl-indan-2-yl)-dipropyl-amine;
(34) (6-methylsulfinyl-indan-2-yl)-dipropyl-amine;
(35) 2-dipropylamino-indan-5-carbaldehyde;
(36) (5-iodo-indan-2-yl)-dipropyl-amine;
(37) (4-iodo-indan-2-yl)-dipropyl-amine;
(38) toluene-4-sulfonic acid 2-dipropylamino-indan-5-yl ester;
(39) toluene-4-sulfonic acid 2-dipropylamino-6-hydroxy-indan-5-yl ester;
(40) N-[2-(benzyl-propylamino)-indan-5-yl]-4-methyl benzene-sulfonamide;
(41) N-[2-(benzyl-propyl-amino)-indan-5-yl]methane-sulfonamide;
(42) 2-[2-(benzyl-propyl-amino)-indan-5-yl]-isoindol-1,3-dione;
(43) benzyl-propyl-(6-pyrrol-1-yl-indan-2-yl)-amine;
(44) propyl-(6-pyrrol-1-yl-indan-2-yl)-amine;
(45) propyl-(6-pyrrolidin-1-yl-indan-2-yl)-amine;
(46) dipropyl-(6-pyrrolidin-1-yl-indan-2-yl)-amine;
(47) cyclopropanecarboxylic acid-[2-(benzyl-propyl-amino)-indan-5-yl] acetamide;
(48) N-[2-(benzyl-propyl-amino)-indan-5-yl]propionamide;
(49) N-[2-(benzyl-propyl-amino)-indan-5-yl]-2,2-dimethyl propionamide;
(50) 5-(2-propenyloxy)-2-(di-N-propylamino)-indan;
(51) 5,6 di-toluenesulfonyloxy-2-(di-N-propylamino)indan;
(52) 5-methanesulfonyloxy-2-(di-N-propylamino)indan;
(53) 5-carbomethoxy-2-(di-N-propylamino)indan;
(54) 5-carboxamido-2-(di-N-propylamino)indan;
(55) 5,6-di-triflurormethansulfonyloxy-2-(propylamino) indan;
(56) 4-methyl-2-(di-N-propylamino)indan;
(57) 4,5-di-methyl-2-(di-N-propylamino)indan;
(58) 5,6-di-methyl-2-(di-N-propylamino)indan;
(59) 5-methyl-2-(di-N-propylamino)indan;
(60) 4-fluoro-2-(N-propyl)aminoindan;
(61) 5-(i-propyl)-2-(di-N-propylamino)indan;
(62) 5-(i-propyl)-2-(N-propylamino)indan;
(63) 4,6-dimethyl-2-(di-N-propylamino)indan;
(64) 4,7-dimethyl-2-(di-N-propylamino)indan;
(65) 5-propyl-2-(di-N-propylamino)indan;
(66) 5-(t-butyl)-2-(dim-propylamino)indan;
(67) 5-trifluoromethyl-2-(di-N-propylamino)indan;
(68) 5-sulfoxamido-2-(di-N-propylamino)indan;
(69) 5-(3-thiophene)-2-(di-N-propylamino)indan;
(70) 5-ethynyl-2-(di-N-propylamino)indan;
(71) 5-acetyl-2-(di-N-propylamino)indan;
(72) 5-cyano-2-(di-N-propylamino)indan;
(73) 5-carbomethoxy-6-acetoxy-2-(di-N-propylamino)indan;
(74) 5-carbomethoxy-6-trifluoromethanesulfonyloxy-2-(di-N-propylamino)indan;
(75) 5-carbomethoxy-6-methoxy-2-(di-N-propylamino) indan;
(76) 5-formyl-6-methoxy-2-(di-N-propylamino)indan;
(77) 5-hydroxymethyl-6-methoxy-2-(di-N-propylamino) indan;
(78) 5-carboxy-6-methoxy-2-(di-N-propylamino)indan;
(79) 5-acetyl-6-methoxy-2-(di-N-propylamino)indan;
(80) 5-carboxamido-6-methoxy-2-(di-N-propylamino)indan;
(81) 5-ethynyl-6-methoxy-2-(di-N-propylamino)indan;
(82) 5-cyano-6-methoxy-2-(di-N-propylamino)indan; and
(83) 5,6-di-(hydroxymethyl-2-(di-N-propylamino)indan.

In some of any of the embodiments described herein, the 2-aminoindan derivative represented by Formula I is any one of the compounds (1)-(13) above, in which the phenyl moiety is substituted by one or two —$OCH_3$, or —$OSO_2CF_3$ groups, or the phenyl moiety bears a —$O(CH_2)_mO$— ring, wherein m is 1 or 2, fused thereto. The structural formulas of compounds 1-13 are depicted in Table A hereinunder.

In exemplary embodiments, the 2-aminoindan derivative used is 5-methoxy-2-aminoindan (Compound 1) or 5,6-dimethoxy-2-aminoindan (Compound 2), the chemical structures of which are depicted hereinbelow.

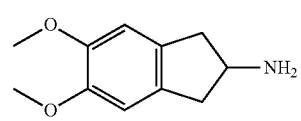

Compound 2

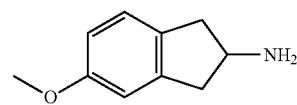

Compound 1

TABLE A

| Compound No. | Name | Structure |
|---|---|---|
| 1 | 5-methoxy-2-aminoindan | 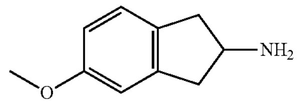 |
| 2 | 5,6-dimethoxy-2-aminoindan | 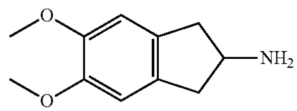 |
| 3 | 5-methoxy-2-(N-propylamino)indan | 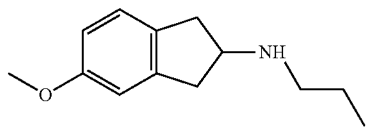 |
| 4 | 5,6-dimethoxy-2-(N-propylamino)indan | 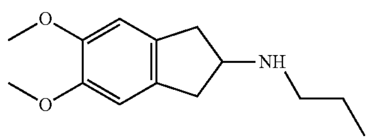 [SMILES: CCCNC1Cc2cc(OC)c(OC)cc2C1] |
| 5 | 5,6-dimethoxy-2-(di-N-butylamino)indan | 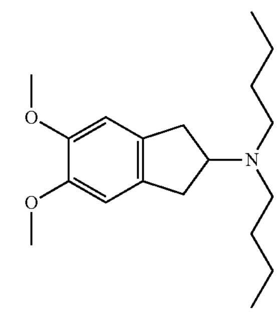 [SMILES: CCCCN(CCCC)C1Cc2cc(OC)c(OC)cc2C1] |
| 6 | 5-(trifluoromethyl-sulfonyloxy)-6-hydroxy-2-(di-N-propylamino)indan | 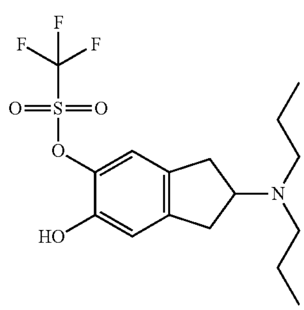 [SMILES: CCCN(CCC)C1Cc2cc(O)c(OS(=O)(=O)C(F)(F)F)cc2C1] |
| 7 | 5-(trifluoromethyl-sulfonyloxy)-2-(N-propylamino)indan | 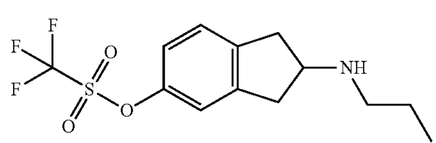 [SMILES: CCCNC1Cc2ccc(OS(=O)(=O)C(F)(F)F)cc2C1] |
| 8 | 5,6-(di-trifluoromethyl—sulfonyloxy)-2-(N-propylamino)indan | 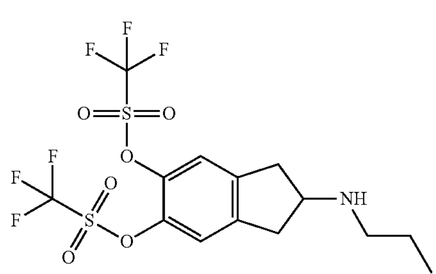 [SMILES: CCCNC1Cc2cc(OS(=O)(=O)C(F)(F)F)c(OS(=O)(=O)C(F)(F)F)cc2C1] |

TABLE A-continued

| Compound No. | Name | Structure |
|---|---|---|
| 9 | 5,6-dimethoxy-2-(pyrrolidino)indan | 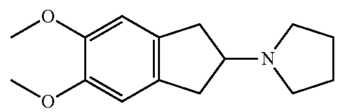 [SMILES: COc1cc2c(cc1OC)CC(N1CCCC1)C2] |
| 10 | 5-(trifluoromethylsulfonyloxy)-6-acetoxy-2-(di-N-propylamino)indan | 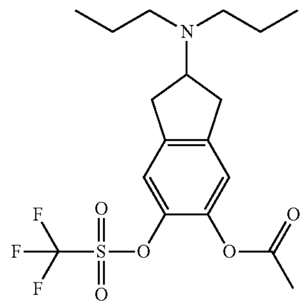 [SMILES: CCCN(CCC)C1Cc2cc(OC(C)=O)c(OS(=O)(=O)C(F)(F)F)cc2C1] |
| 11 | 5-trifluoromethansulfonyloxy-6-methoxy-2-(di-N-propylamino)indan | 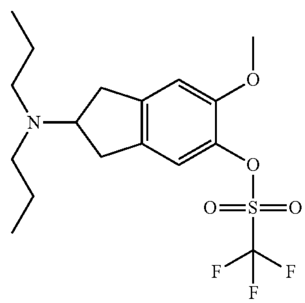 [SMILES: CCCN(CCC)C1Cc2cc(OC)c(OS(=O)(=O)C(F)(F)F)cc2C1] |
| 12 | 5,6-ethylenedioxy-2-(di-N-propylamino)indan | 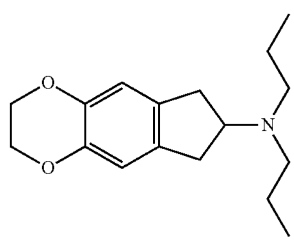 [SMILES: CCCN(CCC)C1Cc2cc3c(cc2C1)OCCO3] |
| 13 | 5,6-methylenedioxy-2-(di-N-propylamino)indan | 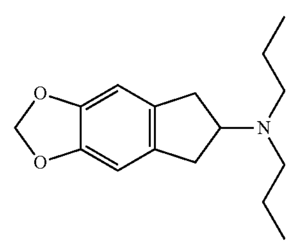 [SMILES: CCCN(CCC)C1Cc2cc3c(cc2C1)OCO3] |

In any one of the embodiments described herein, each of the compounds described herein can be in a form of a pharmaceutically acceptable salt thereof.

As used herein, the phrase "pharmaceutically acceptable salt" refers to a charged species of the parent compound and its counter-ion, which is typically used to modify the solubility characteristics of the parent compound and/or to reduce any significant irritation to an organism by the parent compound, while not abrogating the biological activity and properties of the administered compound.

In the context of some of the present embodiments, a pharmaceutically acceptable salt of the compounds described herein may optionally be an acid addition salt comprising at least one basic (e.g., amine) group of the compound which is in a positively charged form (e.g., an ammonium ion), in combination with at least one counter-ion, derived from the selected acid, that forms a pharmaceutically acceptable salt.

The acid addition salts of the compounds described herein may therefore be complexes formed between one or more basic groups of the drug and one or more equivalents of an acid.

The acid addition salts may include a variety of organic and inorganic acids, such as, but not limited to, hydrochloric acid which affords a hydrochloric acid addition salt, hydrobromic acid which affords a hydrobromic acid addition salt, acetic acid which affords an acetic acid addition salt, ascorbic acid which affords an ascorbic acid addition salt, benzenesulfonic acid which affords a besylate addition salt, camphorsulfonic acid which affords a camphorsulfonic acid addition salt, citric acid which affords a citric acid addition salt, maleic acid which affords a maleic acid addition salt, malic acid which affords a malic acid addition salt, methanesulfonic acid which affords a methanesulfonic acid (mesylate) addition salt, naphthalenesulfonic acid which affords a naphthalenesulfonic acid addition salt, oxalic acid which affords an oxalic acid addition salt, phosphoric acid which affords a phosphoric acid addition salt, toluenesulfonic acid which affords a p-toluenesulfonic acid addition salt, succinic acid which affords a succinic acid addition salt, sulfuric acid which affords a sulfuric acid addition salt, tartaric acid which affords a tartaric acid addition salt and trifluoroacetic acid which affords a trifluoroacetic acid addition salt. Each of these acid addition salts can be either a mono-addition salt or a poly-addition salt, as these terms are defined herein.

In the context of some of the present embodiments, a pharmaceutically acceptable salt of the compounds described herein may optionally be a base addition salt comprising at least one group of the compound which is in a form of an anion, in combination with at least one counter ion (i.e., cation) that forms a pharmaceutically acceptable salt. Examples of suitable cations include metal cations of metals such as, but not limited to, sodium, potassium, magnesium, and calcium or ammonium.

Each of these base addition salts can be either a mono-addition salt or a poly-addition salt, as these terms are defined herein.

Depending on the stoichiometric proportions between the basic or acidic charged group(s) in the compound (e.g., amine group(s)) and the counter-ion in the salt, the acid or base additions salts can be either mono-addition salts or poly-addition salts.

The phrase "mono-addition salt", as used herein, refers to a salt in which the stoichiometric ratio between the counter-ion and charged form of the compound is 1:1, such that the addition salt includes one molar equivalent of the counter-ion per one molar equivalent of the compound.

The phrase "poly-addition salt" as used herein, refers to a salt in which the stoichiometric ratio between the counter-ion and the charged form of the compound is greater than 1:1 and is, for example, 2:1, 3:1, 4:1 and so on, such that the addition salt includes two or more molar equivalents of the counter-ion per molar equivalent of the compound.

Further, in any one of the embodiments described herein, each of the compounds described herein, including the salts thereof, can be in a form of a solvate or a hydrate thereof.

The term "solvate" refers to a complex of variable stoichiometry (e.g., di-, tri-, tetra-, penta-, hexa-, and so on), which is formed by a solute (the 2-aminoindan derivatives described herein) and a solvent, whereby the solvent does not interfere with the biological activity of the solute.

The term "hydrate" refers to a solvate, as defined hereinabove, where the solvent is water.

The present embodiments further encompass any stereoisomers (enantiomers and diastereomers) of the compounds described herein, as well as any isomorph thereof.

The compounds represented by Formula I described herein may be prepared according to methods and practices known in the art, for example, as taught in U.S. Pat. No. 5,708,018.

The term "alcoholic beverage" as used herein encompasses any beverage having an alcoholic content of at least 2% by volume, whether distilled, fortified, brewed, or produced by fermentation, and includes, but is not limited to, wine, beer, fermented liquids derived in whole or in part from fruit juices, such as cider and perry, spirits, flavored alcoholic beverages collectively termed herein and in the art as "alcopops", and the like.

Herein throughout, the term "base liquid" describes a liquid or a liquid form of a substance or a mixture of substances which either alone or when mixed with other additives can form a beverage.

In some embodiments, the base liquid is a base beverage, namely, a liquid or a liquid form of a substance or a mixture of substances which can be used as a beverage per se, or, which, when mixed with alcohol, forms an alcoholic beverage.

In some embodiments, the base beverage is an alcohol-free base beverage.

The phrase "alcohol-free base beverage", as used herein throughout, is a beverage having alcohol percentage that is no more than 50% of the alcohol content in a corresponding alcoholic beverage, preferably no more than 40%, no more than 30%, no more than 20%, no more than 15%, no more than 10%, no more than 5%, no more than 1%, no more than 0.5%, no more than 0.1%, no more than 0.05%, or no more than 0.01%, of the alcohol content acceptable for a certain beverage, including any subranges and any intermediate values there between. This phrase is used herein as encompassing both base beverages that are typically used for forming alcoholic beverages, and base beverages which are typically used per se (e.g., as non-alcoholic beverages, such as juices).

In some embodiments, the alcohol-free base beverage is devoid of alcohol.

By "devoid of" it is meant herein less than 0.01% or less than 0.005%, or less than 0.001%, by volumes, or even null.

In some embodiments, the alcoholic beverage substitutes as described herein are beverages that have residual alcohol content of 0-20% by volume, depending on the alcoholic beverage being substituted.

Exemplary alcohol-free base beverages which form the liquid base for the alcoholic beverage-substitutes described herein include, but are not limited to, natural or artificially flavored fruit juice (such as grape, mango, elder, apple, orange juice, and the like), vegetable juice, fruit syrup, concentrate or nectar from fruits, plant materials such as agave, jello, carbonated beverages such as cola, optionally with addition of roasted malt beer, caffeinated beverages, specialized flavor formulations emulating the taste of existing wines and spirits, non-alcoholic cocktails ("mocktails"), malt beer, dealcoholized ciders, dealcoholized wines, dealcoholized beers, dealcoholized spirits, tonic water and water.

Any combination of the alcohol-free base beverages as described herein is contemplated for the alcoholic beverage substitutes described herein.

In some embodiments, the alcoholic beverage substitute of the invention is selected from a beer-substitute, a wine-substitute, a cider-substitute, a spirit-substitute and an alcopop-substitute beverage.

The term "wine" as used herein and in the art includes the fermented juice of grapes, made in many varieties, such as red, white, sweet, dry, still, and sparkling. Exemplary wine beverages include, but are not limited to, dry red or white wine, semi-dry red or white wine, rose wine, dessert wine, Port wine, Champagne, sparkling wine, and vermouth. Typical alcoholic wine beverages include an alcoholic content of 10-14%.

Herein throughout, whenever a percentage (%) is indicated, volume % of the total volume of the beverage is meant, unless otherwise indicated.

The term "beer" as used herein and in the art means beverages obtained by malting and fermenting one or more of the cereal grains, and includes ale, stout, porter and lager.

The term "spirit" as used herein and in the art refers to distilled alcohol beverages obtained, for example, by distilling starchy material and include, but not limited to, variety of raw grain alcohols, brandies, liquors, saki, Ouzo, arrack, rum, vodka, tequila, schnapps, whiskey, gin, cordial, Cachaça, absinthe, baijiu, cau de vie, soju, aguardiente, pálinka, fernet and slivovitz.

In some embodiments of the present invention, the alcoholic beverage substitute is a beer-substitute.

Exemplary beer-substitutes include, but are not limited to, an ale-substitute, a stout-substitute, a porter-substitute, and a lager-substitute. In some embodiments, such an alcoholic beverage substitute comprises a compound represented by Formula I as described herein in an amount that imparts to the beverage the psychotropic effect, palatability and the pleasures of drinking provided by an alcoholic beer containing 4.8-10% alcohol by volume.

In the beer-substitute beverage described herein, the amount of a 2-aminoindan derivative, for example, compound (1) or (2) defined herein, may be within a range selected from 0.20 mg/ml to 0.70 mg/ml, 0.20 to 0.68 mg/ml, 0.25 to 0.68 mg/ml, 0.28 to 0.66 mg/l, 0.30 to 0.66 mg/ml, 0.28 to 0.65 mg/ml, 0.28 to 0.60 mg/ml 0.30 to 0.60 mg/ml, 0.30 to 0.58 mg/ml, 0.30 to 0.55 mg/ml, 0.30 to 0.50 mg/ml, 0.30 to 0.48 mg/ml, 0.30 to 0.45 mg/ml, 0.30 to 0.42 mg/ml, 0.30 to 0.40 mg/ml, 0.30 to 0.38 mg/ml or 0.31 to 0.36 mg/ml, including any subranges and any intermediate values therebetween.

In some preferred embodiment, the beer-substitute beverage described herein comprises 0.31 mg/ml to 0.33 mg/ml of said compound represented by Formula I.

In some embodiments, the beer substitute beverage contains ethanol in an amount that is more than 0.01% by volume but less than 0.50%, less than 0.25%, less than 0.2%, less than 0.15%, less than 0.10%, or less than 0.05% by volume, including any subranges and any intermediate values therebetween.

In some embodiment, the beer-substitute is devoid of alcohol.

In some embodiments of the present invention, the alcoholic beverage substitute is a wine-substitute.

Exemplary wine-substitutes include, but are not limited to, a dry red wine-substitute, a dry white wine-substitute, a semi-dry red wine-substitute, a semi-dry white wine-substitute, a rose wine-substitute, a dessert wine-substitute, a Port wine-substitute, a Champagne-substitute, a sparkling wine-substitute and vermouth-substitute. In some embodiments, such an alcoholic beverage substitute comprises a compound represented by Formula I as described herein in amount that imparts to the beverage the psychotropic effect, palatability and the pleasures of drinking provided by an alcoholic wine containing 10-14% alcohol by volume.

In the wine-substitute beverage describe herein, the amount of a 2-aminoindan derivative, for example, compound (1) or (2) defined herein, is within a range selected from 0.50 mg/ml to 1.25 mg/ml, 0.55 to 1.25 mg/ml, 0.55 to 1.20 mg/ml, 0.60 to 1.20 mg/l, 0.65 to 1.20 mg/ml, 0.70 to 1.20 mg/ml, 0.70 to 1.10 mg/ml, 0.75 to 1.10 mg/ml, 0.75 to 1.00 mg/ml, 0.78 to 1.00 mg/ml, 0.80 to 1.00 mg/ml, 0.80 to 1.05 mg/ml, 0.80 to 0.98 mg/ml or 0.80 to 0.95 mg/ml, including any subranges and any intermediate values therebetween.

In preferred embodiments, the wine-substitute beverage described herein comprises 0.79 mg/ml to 0.95 mg/ml of said compound represented by Formula I.

In some embodiments, the wine substitute beverage contains ethanol in an amount that is more than 0.01% by volume but less than 5.0%, less than 4.0%, less than 3.0%, less than 2.5%, less than 2.0%, less than 1.5%, less than 1.0%, less than 0.5%, less than 0.25%, less than 0.2%, less than 0.15%, less than 0.10%, or less than 0.05% by volume, including any subranges and any intermediate values therebetween.

In some embodiment, the wine-substitute is devoid of alcohol.

In some embodiments of the present invention, the alcoholic beverage substitute is a spirit-substitute.

Exemplary spirit-substitutes include, but are not limited to, a brandy-substitute, a liquor-substitute, saki-substitute, Ouzo-substitute, an arrack-substitute, a rum-substitute, a vodka-substitute, a tequila-substitute, a schnapps-substitute, a whiskey-substitute, a gin-substitute, a cordial-substitute, Cachaça-substitute and a slivovitz-substitute, comprising a compound represented by Formula I as described herein in an amount that imparts to the beverage the psychotropic effect, palatability and the pleasures of drinking provided by an alcoholic spirit containing 30-40% alcohol by volume.

In the spirit-substitute beverage described herein, the amount of a 2-aminoindan derivative, for example, compound (1) or (2) defined herein, is within a range selected from 1.90 mg/ml to 2.97 mg/ml, 1.90 mg/ml to 2.64 mg/ml 1.90 mg/ml to 2.60 mg/ml, 1.90 to 2.55 mg/ml, 1.95 to 2.55 mg/ml, 1.95 to 2.50 mg/ml, 1.95 to 2.40 mg/ml, 1.95 to 2.30 mg/ml, 1.96 to 2.35 mg/l, 1.96 to 2.30 mg/ml, 1.96 to 2.28 mg/ml, 1.96 to 2.25 mg/ml, 1.96 to 2.20 mg/ml, 1.98 to 2.28 mg/ml, 1.98 to 2.25 mg/ml, or 1.98 to 2.20 mg/ml, including any subranges and any intermediate values therebetween.

In preferred embodiments, the spirit-substitute beverage described herein comprises 1.98 mg/ml to 2.20 mg/ml of said compound represented by Formula I as described herein.

In some embodiments, the spirit-substitute beverage contains ethanol in an amount that is more than 0.01% but less than 15%, less than 14%, less than 12%, less than 11.0%, less than 10.0%, less than 9.0%, less than 8.0%, less than 7.0%, less than 6.0%, less than 4.50%, less than 4.00%, less than 3.50%, less than 3.00%, less than 2.50%, less than 2.00%, less than 1.50%, less than 1.00%, less than 0.50%, less than 0.25%, less than 0.2%, less than 0.15%, or less than 0.10%, by volume, including any subranges and any intermediate values therebetween.

In some embodiments, the spirit-substitute is an alcohol-free beverage as defined herein.

In some embodiments of the present invention, the alcoholic beverage substitute is an alcopop-substitute.

Alcopop beverages, also termed herein and in the art "coolers" or "spirit coolers", are flavored alcoholic beverages or flavored malt beverages based on fruit juice or nectar, and/or a variety of naturally and/or artificially flavored syrups. Exemplary alcopop beverages include, but are not limited to (i) a malt beverage, designate herein "a beer cooler", containing a malt base or beer and at least 5% by volume of added natural or artificial blending material, such as fruit juice, flavors, flavorings, colorings, and, optionally, preservatives; (ii) a wine cooler which is a beverage containing wine and more than 15% by volume of added natural or artificial blending material, such as fruit juices, flavors, flavorings, adjuncts, water (plain, carbonated, or sparkling), colorings, and, optionally, preservatives; and (iii) a beverage designated herein "a spirit cooler", containing distilled alcohol, and added natural or artificial blending material, such as fruit juices, flavors, flavorings, colorings, and, optionally, preservatives.

Alcopop brands are numerous and their alcoholic base varies greatly. Most alcopop beverages contain 4-7% alcohol by volume, and some may even contain as much as 12.5% alcohol by volume. Some notable brands include, but are not limited to, Smirnoff Ice, Mike's Hard Lemonade, Bacardi Breezer, Skyy Blue, Jack Daniel's Hard Cola, WKD Original Vodka, Six Degrees and MG Spirits.

In some embodiments, such an alcoholic beverage substitute comprises a compound represented by Formula I as described herein in an amount that imparts to the beverage the psychotropic effect, palatability and the pleasures of drinking provided by an alcoholic alcopop containing 4-7% alcohol by volume.

In the alcopop-substitute beverage described herein, the amount of a 2-aminoindan derivative, for example, compound (1) or (2) defined herein, may be within a range selected from 0.25 to 0.60 mg/ml, 0.28 to 0.60 mg/l, 0.30 to 0.60 mg/ml, 0.28 to 0.58 mg/ml, 0.28 to 0.55 mg/ml 0.30 to 0.55 mg/ml, 0.30 to 0.50 mg/ml, 0.30 to 0.48 mg/ml, 0.30 to 0.45 mg/ml, 0.30 to 0.42 mg/ml, 0.30 to 0.40 mg/ml, 0.30 to 0.38 mg/ml or 0.31 to 0.36 mg/ml, including any subranges and any intermediate values therebetween.

In some preferred embodiment, the alcopop-substitute beverage described herein comprises 0.31 mg/ml to 0.33 mg/ml of said compound represented by Formula I.

In some embodiments, the alcopop substitute beverage contains ethanol in an amount that is more than 0.01% by volume but less than 1.00%, less than 0.70%, less than 0.50%, less than 0.25%, less than 0.2%, less than 0.15%, less than 0.10%, or less than 0.05% by volume, including any subranges and any intermediate values therebetween.

In some embodiment, the alcopop-substitute is completely devoid of alcohol.

In some of any of the embodiments of the present invention, the alcoholic beverage substitute optionally contains alcohol (ethanol), yet in an amount that is no more than 50% of the ethanol content acceptable for a certain kind of a corresponding alcoholic beverage (the alcoholic beverage that is intended to be substituted). In the context of these embodiments, the beverage is an alcohol-reduced beverage. In some embodiments, the alcohol-reduced beverage contains alcohol in an amount of 20-50%, 20-40%, 20-30%, or 30-40% of the amount of alcohol in a corresponding alcoholic beverage. In exemplary embodiments the alcohol-reduced beverage is selected from an alcohol-reduced spirit, having alcohol content of about 11% to about 20% by volume, an alcohol-reduced wine beverage that has a reduced alcohol content of about 3% to about 7.5% by volume, an alcohol-reduced beer beverage that has a reduced alcohol content of about 0.5% to about 2.5% by volume or about 2.5% to about 5.0% by volume, or an alcohol-reduced alcopop beverage that has a reduced alcohol content of about 0.5% to about 2.5% or 2.5% to about 5.0% by volume.

In some exemplary embodiments, the alcohol-reduced beer beverage contains ethanol in an amount that is more than 0.5% but less than 5.00%, less than 4.50%, less than 4.00%, less than 3.50%, less than 3.00%, less than 2.50%, less than 2.00%, less than 1.50%, or less than 1.00%, by volume, including any subranges and any intermediate values therebetween.

In some exemplary embodiments, the alcohol-reduced wine beverage contains ethanol in an amount that is more than 3.0% but less than 7.0%, less than 6.5%, less than 6.0%, less than 5.0%, less than 5.5%, less than 5.0%, less than 4.5%, less than 4.0%, or less than 3.5%, by volume, including any subranges and any intermediate values there between.

In some exemplary embodiments, the alcohol-reduced spirit beverage contains ethanol in an amount that is more than 11.0% but less than 20.0%, less than 18.0%, less than 16.0%, less than 14.0%, less than 15.0%, less than 14.0%, less than 13.5%, less than 13.505%, less than 12.5%, or less than 12.0%, by volume, including any subranges and any intermediate values therebetween.

In some exemplary embodiments, the alcohol-reduced alcopop beverage contains ethanol in an amount that is more than 0.5% but less than 5.00%, less than 4.50%, less than 4.00%, less than 3.50%, less than 3.00%, less than 2.50%, less than 2.00%, less than 1.50%, or less than 1.00%, by volume, including any subranges and any intermediate values there between.

In some of any one of the embodiments of the present invention, optionally or additionally, the base liquid or base beverage is formulated to include additives, such as flavoring agents, colorants, odoriferous agents, $CO_2$ and/or other additives such as viscosity modifying agents, foaming agents, antifoaming agents, and preservatives that account for the taste and texture of wine or beer or spirit, such that the substitute beverage will contain at least part or all the ingredients used to form the corresponding alcoholic beverages, except for the alcohol content therein. Preferably, additives used in the alcohol-substitute and alcohol reduced beverages described herein are FDA-approved, and/or edible. In some embodiments, the additives are selected as soluble in the base beverage or base liquid.

The phrases "flavoring agent" and "odoriferous agent", as used herein, describe a class of substances which are added to edible products in order to induce a certain flavor or smell in the product, and are commonly referred to also as "flavorants". Flavorants can be synthetic or natural extracts, which are extracted from a source substance. Typical flavorants are specific and often complex mixtures of singular naturally occurring or synthetic flavor compounds combined together to either imitate or enhance a natural flavor. Many flavorants are esters, which can be characterized by a typical flavor, such as, for some non-limiting examples, diacetyl which gives a buttery flavor, isoamyl acetate that is perceived as banana, cinnamic aldehyde which is the basis for the typical flavor of cinnamon, ethyl propionate is perceived as fruity, limonene is perceived as orange, ethyl-(E, Z)-2,4-decadienoate is perceived as pear, allyl hexanoate is perceived as pineapple, ethyl maltol, is perceived as sugar or cotton candy, methyl salicylate is known as the wintergreen flavor, and benzaldehyde is perceived as bitter almond.

In some embodiments, the flavoring agent used is of a natural source and can be, for example, an extract of a fruit, a vegetable, a herb or of any other edible substance, a fruit juice or a vegetable juice, or any combination thereof. Such natural flavoring agents are often considered also as providing an added nutritional value to an alcohol-substitute beverage containing same.

The term "colorant", as used herein, refers to any natural or synthetic coloring substance, and describes any substance that is added to food or drink in order to alter its color. Exemplary usable colorants include, but are not limited to, synthetic colorants such as FD&C Blue No. 1—Brilliant Blue FCF (E133), FD&C Blue No. 2—Indigotine (E132), FD&C Green No. 3—Fast Green FCF (E143), FD&C Red No. 40—Allura Red AC (E129), FD&C Red No. 3—erythrosine (E127), FD&C Yellow No. 5—tartrazine (E102), and FD&C Yellow No. 6—Sunset Yellow FCF (E110), and natural food colorants such as carmine (E120), enocianin (E163), black carrot (E163), paprika (E160c), annatto (E160b), beta carotene (E160a), lutein (E161b), riboflavin (E101), curcumin (E100), copper chlorophyllin (E141), chlorophyll (E140), caramel (E150), and extracts of foodstuffs such as elderberry, aronia, grape, beetroot, carrot, turmeric (tumeric) root, spinach, stinging nettle and burnt sugar (caramelized sugar).

The term "preservative", as used herein, describes a synthetic or natural additive substance that is added to edible products in order to prevent or retard chemical and biochemical decomposition of the product by oxygen, moisture and/or microbes. Exemplary anti-microbial preservatives include, but are not limited to, calcium propionate, sodium nitrate, sodium nitrite, sulfites (sulfur dioxide, sodium bisulfite, potassium hydrogen sulfite, etc.) and disodium EDTA, sodium benzoate, potassium sorbate. Natural substances that retard microorganisms growth include lactic acid, salt, sugar and vinegar.

Exemplary antioxidant preservatives include, but are not limited to, butylated hydroxyanisole (BHA) and butylated hydroxytoluene (BHT). Natural antioxidants include, but are not limited to, herbal extracts such as rosemary and oregano, and vitamins such as Vitamin E and Vitamin C (ascorbic acid)

The phrase "foaming agent" as used herein, describes an edible surfactant, which when present in small amounts, facilitates the formation of a foam, or enhances its colloidal stability by inhibiting the coalescence of bubbles. Exemplary foaming agents include, without limitation, sodium laureth/lauryl sulfate (SLS), sodium lauryl ether sulfate (SLES) and ammonium lauryl sulfate (ALS).

The phrase "antifoaming agent" as used herein, describes an edible substance that inhibits the formation of foam and curbs effusion or effervescence in edible products. An exemplary antifoaming agent is polydimethylsiloxane.

The phrases "viscosity modifying agent" or "thickener" as used herein are interchangeable and describe agents that enables to control the viscosity of the beverages described herein. Exemplary thickeners include, but are not limited to, starch-based thickeners such as maltodextrin and gum-based thickeners such as xanthan or cellulose gum.

In some of any of the embodiments of the present invention, natural or artificial flavourings and taste-improving additives may be added to the alcoholic beverage substitutes described herein. Non-limiting examples include fruit flavours, preferably natural flavours, such as elder, grape, orange, ginger, red apple or lemon grass. Artificial or synthetic flavourings include, but are not limited to, cola flavours, ice cream flavors, anise flavor, amaretto flavor. These additives are added in addition to or instead of those found in the alcoholic beverage, if indeed present therein.

In some embodiments, any one of the alcohol-free base beverages described herein, for example, non-alcoholic beverages, is made an "alcoholic-like" beverage in terms of the psychotropic effect it imparts, e.g., intoxication, palatability and the pleasures of drinking, by mixing the base beverage with an amount of a 2-aminoindan derivative, as described herein, that would account for alcohol (corresponds in its effect to an effect of) in an amount of 2% to 30% or more, for example, 2%, 3%, 5%, 8%, 10%, 12%, 15%, 18%, 20%, 30%, or more. In exemplary embodiments, the amount of a compound represented by Formula I as described herein, added to the base beverage is in the range selected from 0.20 mg/ml to 2.97 mg/ml, 0.20 mg/ml to 0.70 mg/ml, 0.28 to 0.65 mg/ml, 0.30 to 0.60 mg/ml, 0.30 to 0.55 mg/ml, 0.30 to 0.50 mg/ml, 0.30 to 0.45 mg/ml, 0.30 to 0.40 mg/ml, 0.31 to 0.36 mg/ml, 0.50 to 1.25 mg/ml, 0.55 to 1.20 mg/ml, 0.60 to 1.20 mg/ml, 0.70 to 1.20 mg/ml, 0.70 to 1.10 mg/ml, 0.75 to 1.00 mg/ml, 0.80 to 1.00 mg/ml, 0.80 to 1.05 mg/ml, 0.80 to 0.95 mg/ml, 1.25 to 1.90 mg/ml, 1.25 to 2.00 mg/ml, 1.90 to 2.97 mg/ml, 1.90 mg/ml to 2.60 mg/ml, 1.95 to 2.55 mg/ml, 1.95 to 2.50 mg/ml, 1.95 to 2.40 mg/ml, 1.96 to 2.30 mg/ml, 1.96 to 2.25 mg/ml, 1.98 to 2.25 mg/ml, or 1.98 to 2.20 mg/ml.

Exemplary alcohol-free base beverages that can be made into alcohol-like beverages by addition of a compound represented by Formula I as described herein include, but are not limited to, fruit juice, fruit syrup, concentrate or nectar from fruits, jello, vegetable juice, plant materials such as agave, carbonated beverages such as cola, caffeinated beverages, malt beer, tonic water and water. Alcopop substitutes, for example, are made by adding the aminoindan derivative to fruit juices containing flavors, flavorings, colorings, and, optionally, preservatives, etc., instead of the alcoholic component.

In some of any of the embodiments of the present invention, the alcoholic beverage substitute may be obtained from a dealcoholized beverage such as beer or wine or even a distilled alcoholic (spirit) beverage, which were dealcoholized using any of the methods known in the art, for example boiling as taught in U.S. Pat. No. 1,390,710, or using heated steam as taught in U.S. Pat. No. 1,256,894, or using porous, hydrophobic solid (such as zeolite or a monolithic microporous solid) to specifically adsorb ethanol, as taught in U.S. Pat. No. 6,472,009. Reconstituted dealcoholized beverages retain as much as possible of the original drinking experience.

In some of these embodiments, an aminoindan derivative compound represented by Formula I as described herein is added to the dealcoholized beverage in an amount that corresponds to the original alcohol percentage of the alcoholic beverage, along with flavor- and sense-essential elements that replace the original elements in the alcoholic beverage which were removed or reduced in the dealcoholization process.

Such added ingredients include, for example, small quantities of volatile acids, such as formic acid, acetic acid and propionic acid, which replace the naturally contained volatile acids of the beverages removed or destroyed, e.g., due to boiling in a dealcoholization process, as described, for example in U.S. Pat. No. 1,401,700. In reconstructing the taste and flavor of the original alcoholic beer or wine beverage, a small proportion of volatile acid or a mixture of volatile acids is added to the cooled dealcoholized beverage. In the treatment of dealcoholized beer, for example, the proportion of volatile acetic acid that may be added is approximately 12.3 mg per 100 ml of dealcoholized beer, or in the case of formic, propionic and butyric acids or mixtures thereof with or without acetic acid, the equivalent of this quantity, provided that the amount of volatile acid added does not exceeds 0.05% by weight. It is assumed that the addition of the volatile acids in the amounts described herein has a marked preserving effect upon the beverage, similar to that produced by the alcohol in natural alcoholic fermented beverages.

In some embodiments, the beverage may be perfected as described, for example, in U.S. Pat. No. 1,302,551, by adding fermentable matter and live yeast, for example, fermenting wort in the case of dealcoholized beer, and causing fermentation to proceed without carbonating the beverage, thereby promoting yeast propagation. According to some of these embodiments, the volatile acid may be added after the yeast fermentation has been completed and before artificial carbonation.

In some embodiments in which a wine-substitute beverage is obtained from a dealcoholized wine, tryptophan and cliousclatine, that act as psychotropic agents that give individuals the pleasures of drinking wine, may be added.

The palatability, and particularly the "smoothness" of some alcoholic-substitute beverages described herein, particularly non-alcoholic substitutes of whiskies, brandies, cordials, liqueurs, and especially gins, may be improved by the addition of polyhydric alcohols having three or more hydroxyl groups. Thus, in some embodiments of the invention, glycerine is added to the spirit substitute, and in preferred embodiments thereof, polyhydric alcohols having more than three hydroxyl groups, such as sorbitol, are added to impart the desired smoothness to the non-alcoholic beverage substitute. In some embodiments, a technical sorbitol, which is produced by the reduction of glucose and which contains, in addition to sorbitol, moisture, other polyhydric alcohols, small amounts of ash, sugar, organic acids, and other impurities, is added so as to significantly improve the palatability and smoothness of the spirit-substitute beverage. Other polyhydric alcohols having more than three hydroxyl groups that are used in some embodiments of the present invention, either alone or mixed with sorbitol and/or glycerine are mannitol, iditol and galactitol (dulcitol), or any mixtures thereof or any mixtures of these with any other desired substances used as modifiers or diluents, or otherwise improve the finished product. In exemplary embodiments, sorbitol is added to a wine-substitute beverage of the invention, in amounts higher than its normal content in alcoholic wine for the purpose of improving palatability of the beverage.

In some alternative embodiments, salts of glycine and alanine are used for improving the smoothness, mellowness and flavor of wine or spirit substitutes. Addition of 0.01-6.0% (w/v) of citrate, tartrate and cyclamate salts of glycine and alanine is known to imitate the effect of long aging of wines and whiskies, as taught, for example in U.S. Pat. No. 3,558,325.

After addition, for example, of the volatile acid, fermentable matter and live yeast, tryptophan, cliousclatine or polyhydric alcohols to the reconstructed dealcoholized beverage, it is preferred that the latter be stored for a 0.5-3 months period at a low temperature, since under these conditions an improvement in the flavor, taste and bouquet of the beverage takes place, apparently by an esterifying action of the volatile acids in the presence of the various enzymes contained in the beverage, particularly when perfected by a secondary yeast propagation. At the termination of a suitable period of time, for example, in the case of dealcoholized beer, two weeks at a temperature of 10 to 15° C., the esterifying or aging action will have been carried to a sufficient extent and the beverage may be prepared for the market.

The alcoholic beverage-substitutes described herein may be contained in any of the known containers applied for alcoholic drinks or beverages in general, for example, a 330 ml, 500 ml, 750 ml and 1 liter bottle or tin, or in a barrel. The stability of the alcoholic beverage substitute obtained according to any of the embodiments of the present invention is preferably more than 365 days at room temperature, and it may be stored for up to 999 days at 10° C.

In an aspect of some embodiments of the present invention there is provided a process for the preparation of an alcoholic beverage substitute. The process comprises mixing an alcohol-free base beverage as defined herein with an amount of a compound represented by Formula I as described herein that accounts for the psychotropic and palatability effects imparted by an alcoholic beverage. In some embodiments, the alcoholic beverage substitute is a beer-substitute, a wine-substitute, a spirit substitute, cider-substitute or an alcopop substitute as described herein.

In exemplary embodiments, the process described herein is for the preparation of an alcohol-reduced beverage as described herein.

In some embodiments, an alcoholic-like beverage is produced by mixing an alcohol-free base beverage as described herein with an amount of a compound represented by Formula I as described herein that accounts for the psychotropic and palatability effects imparted by alcohol in the amount of 2% to 30% by volume.

It is expected that during the life of a patent maturing from this application many relevant base liquids and respective beverages will be developed and the scope of the terms "base liquid" and "beverage" is intended to include all such new technologies a priori.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "10 μm" is intended to mean "about 10 μm".

As used herein, numerical ranges preceded by the term "about" should not be considered to be limited to the recited range. Rather, numerical ranges preceded by the term "about" should be understood to include a range accepted by those skilled in the art for any given element in microcapsules or formulations according to the present invention.

The term "about" as used herein means within an acceptable error range for a particular value as determined by one of ordinary skill in the art, which will depend in part on how the value is measured or determined, i.e., the limitations of the measurement system. For example, "about" can mean a range of up to 10%, more preferably up to 5%, and still more preferably up to 1% of a given value. Where particular values are described in the application and claims, unless otherwise stated, the meaning of the term "about" is within an acceptable error range for the particular value.

The terms "comprises", "comprising", "includes", "including", "having" and their conjugates mean "including but not limited to".

The term "consisting of" means "including and limited to".

The term "consisting essentially of" means that the composition, method or microcapsules may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "alkyl" refers to a saturated aliphatic hydrocarbon including straight chain and branched chain groups. Preferably, the alkyl group has 1 to 20 carbon atoms. Whenever a numerical range; e.g., "1-20", is stated herein, it implies that the group, in this case the alkyl group, may contain 1 carbon atom, 2 carbon atoms, 3 carbon atoms, etc., up to and including 20 carbon atoms. More preferably, the alkyl is a medium size alkyl having 1 to 10 or 1 to 8 carbon atoms. Most preferably, unless otherwise indicated, the alkyl is a lower alkyl having 1 to 8 carbon atoms.

An "alkenyl" group refers to a partially unsaturated hydrocarbon including straight chain and branched chain groups, which consists of at least two carbon atoms and at least one carbon-carbon double bond. Preferably, the alkenyl is a medium size alkenyl having 2 to 10 or 2 to 8 carbon atoms. Most preferably, unless otherwise indicated, the alkenyl is a lower alkenyl having 2 to 4 carbon atoms. Non-limiting examples of alkenyl include ethenyl (vinyl), propenyl, butenyl, pentenyl and hexenyl.

An "alkynyl" group refers to an a partially unsaturated hydrocarbon including straight chain and branched chain groups, which consists of at least two carbon atoms and at least one carbon-carbon triple bond. Preferably, the alkynyl is a medium size alkynyl having 2 to 10 or 2 to 8 carbon atoms. Most preferably, unless otherwise indicated, the alkynyl is a lower alkynyl having 2 to 8 carbon atoms. Non-limiting examples of alkynyl include ethynyl, propynyl, butynyl, pentynyl and hexynyl.

A "cycloalkyl" group refers to a saturated, all-carbon monocyclic or polycyclic (fused ring, i.e., rings which share an adjacent pair of carbon atoms) group, having 3 to 20, preferably 3 to 8 carbon atoms. Examples, without limitation, of cycloalkyl groups are cyclopropane, cyclobutane, cyclopentane, cyclohexane and cycloheptane.

An "aryl" group refers to an all-carbon monocyclic or polycyclic (fused-ring i.e., rings which share adjacent pairs of carbon atoms) groups having a completely conjugated pi-electron system. Examples, without limitation, of aryl groups are phenyl, naphthalenyl and anthracenyl.

A "heteroaryl" group, as used herein, refers to a monocyclic or polycyclic (fused ring, i.e., rings which share an adjacent pair of atoms) group having in the ring(s) one or more heteroatoms, selected from nitrogen, oxygen and sulfur and, in addition, having a completely conjugated pi-electron system. Examples, without limitation, of heteroaryl groups include pyrrole, furan, thiophene, imidazole, oxazole, thiazole, pyrazole, pyridine, pyrimidine, quinoline, isoquinoline, phthalimide, and purine.

A "heteroalicyclic" group as used herein refers to a monocyclic or polycyclic (namely, a fused ring group as defined herein) having in the ring(s) one or more atoms such as nitrogen, oxygen and sulfur. The rings may also have one or more double bonds. However, the rings do not have a completely conjugated pi-electron system. Representative examples are piperidine, piperazine, tetrahydro furane, tetrahydropyrane, morpholine, pyrroline and the like.

As used herein, the term "hydroxyalkyl" refers to an alkyl, as this term is defined herein, substituted by an OH group, and includes, for example, hydroxymethyl, hydroxyethyl, hydroxypropyl and hydroxy-n-butyl.

As used herein the term thienyl refers to the radical:

As used herein, the term "halogen", which is also referred to herein interchangeably as "halo", includes chloro (Cl), bromo (Br), iodo (I) and fluoro (F).

Any of the alkyl, alkenyl, alkynyl, cycloalkyl, heteroaryl, heteroclicylic or aryl group as defined herein may be substituted or unsubstituted. When substituted, the substituent group can be, for example, alkyl, —O—($C_1$-$C_8$)alkyl, —O—($C_3$-$C_8$)cycloalkyl, trihaloalkyl, hydroxyalkyl, ($C_3$-$C_8$) cycloalkyl, alkenyl, alkynyl, aryl, heteroaryl, heteroalicyclic, halo, OH, O-aryl, —SH, —S—($C_1$-$C_8$)alkyl, —S—($C_3$-$C_8$)cycloalkyl, —S-aryl, —O—S═O, —S(═O)$_2$—R', —CN, —NO$_2$, —O—P(═O)(OR')(OR''), —PR'R'', —C(═O)—R', —C(═S)—R', —C(═O)—O—R', —C(═S)—O—R', —OC(═O)—NR'R'', —OC(═S)—NR'R'', —OC(═S)—NR'R'', —S(═O)$_2$—NR'R'', and —NR'R'', where R' and R'', each independently, is hydrogen, alkyl, alkenyl, cycloalkyl, aryl, heteroaryl (bonded through a ring carbon) or heteroalicyclic (bonded through a ring carbon), as these terms are defined herein.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:
1. An alcoholic beverage-substitute comprising a base liquid and 5-methoxy-2-aminoindan or a physiologically acceptable salt thereof,
wherein the base liquid is a dealcoholized spirit, a dealcoholized beer, or a dealcoholized wine, and when the base liquid is a dealcoholized spirit the 5-methoxy-2-aminoindan is in an amount that imparts to the alcoholic beverage-substitute the psychotropic effect, palatability and pleasures of drinking provided by an alcoholic spirit containing 30-40% alcohol by volume, the amount being in a range of from 1.90 mg/ml to 2.97 mg/ml;

when the base liquid is a dealcoholized beer the 5-methoxy-2-aminoindan is in an amount that imparts to the alcoholic beverage-substitute the psychotropic effect, palatability and the pleasures of drinking provided by an alcoholic beer containing 4.8-10% alcohol by volume, the amount being in a range of from 0.20 mg/ml to 0.70 mg/ml; and when the base liquid is a dealcoholized wine the 5-methoxy-2-aminoindan is in an amount that imparts to the alcoholic beverage-substitute the psychotropic effect, palatability and the pleasures of drinking provided by an alcoholic wine containing 10-14% alcohol by volume, the amount being in a range of from 0.50 mg/ml to 1.25 mg/ml.

2. The alcoholic beverage-substitute according to claim 1, wherein the dealcoholized beer comprises ethanol in an amount that is more than 0.01% by volume but less than 0.50% by volume.

3. The alcoholic beverage-substitute according to claim 1, wherein the dealcoholized wine comprises ethanol in an amount that is more than 0.01% by volume but less than 5.0% by volume.

4. The alcoholic beverage-substitute according to claim 1, wherein the dealcoholized spirit comprises ethanol in an amount that is more than 0.01% but less than 15% by volume.

5. A process for the preparation of an alcoholic beverage-substitute according to claim 1, the process comprising mixing the base liquid with 5-methoxy-2-aminoindan or a physiologically acceptable salt thereof.

6. The process according to claim 5, further comprising adding to the base liquid at least one of a flavoring agent, a colorant, an odoriferous agent, $CO_2$, a viscosity modifying agent, a foaming agent, an antifoaming agent, or a preservative.

7. An alcoholic beverage-substitute comprising a base liquid and 5-methoxy-2-aminoindan or a physiologically acceptable salt thereof, wherein, the alcoholic beverage-substitute is an alcoholic spirit substitute, the base liquid comprises a dealcoholized spirit and the 5-methoxy-2-aminoindan is in an amount that imparts to the beverage the psychotropic effect, palatability and the pleasures of drinking provided by an alcoholic spirit containing 30-40% alcohol by volume, the amount being in a range of from 1.90 mg/ml to 2.97 mg/ml.

8. The alcoholic beverage-substitute according to claim 7, wherein the spirit-substitute comprises ethanol in an amount that is more than 0.01% but less than 15% by volume.

9. A process for the preparation of an alcoholic beverage-substitute according to claim 7, the process comprising mixing the base liquid with 5-methoxy-2-aminoindan or a physiologically acceptable salt thereof.

10. The process according to claim 9, further comprising adding to the base liquid at least one of a flavoring agent, a colorant, an odiferous agent, $CO_2$, a viscosity modifying agent, a foaming agent, an antifoaming agent, or a preservative.

11. An alcoholic beverage-substitute comprising a base liquid and 5-methoxy-2-aminoindan or a physiologically acceptable salt thereof, wherein the base liquid is an alcohol-reduced alcopop and the 5-methoxy-2-aminoindan is in an amount that imparts to the alcoholic beverage-substitute the psychotropic effect, palatability and the pleasures of drinking provided by an alcopop beverage containing 4.5-12.5% alcohol by volume, the amount being in a range from 0.25 to 0.60 mg/ml, and wherein the alcohol-reduced alcopop comprises ethanol in an amount that is more than 0.5% but less than 1.00% by volume.

\* \* \* \* \*